US009446152B2

(12) United States Patent
Mattoussi et al.

(10) Patent No.: US 9,446,152 B2
(45) Date of Patent: Sep. 20, 2016

(54) POLYETHYLENE GLYCOL BASED OLIGOMERS FOR COATING NANOPARTICLES, NANOPARTICLES COATED THEREWITH, AND RELATED METHODS

(71) Applicant: The Florida State University Research Foundation, Inc., Tallahassee, FL (US)

(72) Inventors: Hedi Mattoussi, Tallahassee, FL (US); Goutam Palui, Tallahassee, FL (US); Hyon Bin Na, Seoul (KR)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 14/838,586

(22) Filed: Aug. 28, 2015

(65) Prior Publication Data
US 2016/0136302 A1    May 19, 2016

Related U.S. Application Data

(60) Division of application No. 13/772,595, filed on Feb. 21, 2013, now Pat. No. 9,150,748, which is a continuation-in-part of application No. 13/608,119, filed on Sep. 10, 2012, now abandoned.

(60) Provisional application No. 61/532,756, filed on Sep. 9, 2011.

(51) Int. Cl.
| | |
|---|---|
| A61K 49/00 | (2006.01) |
| H01F 1/00 | (2006.01) |
| C08F 8/32 | (2006.01) |
| C08F 20/06 | (2006.01) |
| C08F 22/00 | (2006.01) |
| C08K 5/00 | (2006.01) |
| C08K 5/13 | (2006.01) |
| C08L 33/00 | (2006.01) |
| C08L 71/08 | (2006.01) |
| C09D 133/14 | (2006.01) |
| C08F 220/26 | (2006.01) |

(52) U.S. Cl.
CPC ............ *A61K 49/0067* (2013.01); *C08F 8/32* (2013.01); *C08F 20/06* (2013.01); *C08F 22/00* (2013.01); *C08K 5/00* (2013.01); *C08K 5/13* (2013.01); *C08L 33/00* (2013.01); *C08L 71/08* (2013.01); *C09D 133/14* (2013.01); *H01F 1/0054* (2013.01); *C08F 220/26* (2013.01)

(58) Field of Classification Search
CPC ... A61K 49/0067; H01F 1/0054; C08F 8/32; C08F 30/06; C08F 22/00; C08F 220/26; C08K 5/00; C08K 5/13; C08L 33/00; C08L 71/08; C09D 133/14

USPC .......... 524/403, 330, 24, 45, 214, 226, 315, 524/502, 503, 535; 526/317.1, 318, 318.43, 526/320; 525/183, 182, 185
See application file for complete search history.

(56) References Cited

PUBLICATIONS

M. Stewart et al. "Multidentate Poly(ethylene glycol) Ligands Provide Colloidal Stability to Semiconductor and Metallic Nanocrystals in Extreme Conditions", J. Am. Chem. Soc., 2010, 132 (28), pp. 9804-9813.*
W. Liu et al. "Compact Biocompatible Quantum Dots via RAFT-Mediated Synthesis of Imidazole-Based Random Copolymer Ligand", J. Am. Chem. Soc., 2010, 132, pp. 472-483.*
Alivisatos, A.P., Semiconductor Clusters, Nanocrystals, and Quantum Dots, Science; Feb. 16, 1996, vol. 271, No. 5251; ProQuest; pp. 933-937.
Murray, C. B., et al., Synthesis and Characterization of Monodisperse Nanocrystals and Close-Packed Nanocrystal Assemblies, Annu. Rev. Mater. Sci, 2000, vol. 30 pp. 545-610.
Klimov, V.I. et al., Optical Gain and Stimulated Emission in Nanocrystal Quantum Dots, Science, Oct. 13, 2000, vol. 290, No. 5490; ProQuest, pp. 314-317.
Malko, A.V. et al., From amplified spontaneous emission to microring lasing using nanocrystal quantum dots solids, Applied Physcis Letters, Aug. 12, 2002, vol. 81, No. 7, pp. 1303-1305.
Nozik, A. J. et al., Semiconductor Quantum Dots and Quantum Dot Arrays and Applications of Multiple Exciton Generation to Third-Generation Photovoltaic Solar Cells, Chem. Rev., 2010, vol. 110, pp. 6873-6890.
Li Ling et al., Highly Efficient CdS Quantum Dot-Sensitized Solar Cells Based on a Modified Polysulfide Electrolyte, Journal of the American Chemical Society, 2011, vol. 133, pp. 8458-8460.
Raymo, Francisco M., et al., Luminescent chemosensors based on semiconductor quantum dots, Physical Chemistry Chemical Physics, Feb. 1, 2007, vol. 9, pp. 2036-2043.
Medintz, Igor L., et al., Quantum dot bioconjugates for imaging labelling and sensing, Nature Materials, Jun. 2005, vol. 4, pp. 435-446.
Michalet, X. et al., Quantum Dots for Live Cells, in Vivo Imaging, and Diagnostics, Science, Jan. 28, 2005, vol. 307, pp. 538-544.

(Continued)

*Primary Examiner* — Michael M Bernshteyn
(74) *Attorney, Agent, or Firm* — Armstrong Teasdale LLP

(57) ABSTRACT

In a composition aspect of the invention, a nanoparticle coating comprises repeating polyacrylic acid monomers covalently bound together in an aliphatic chain having a plurality of carboxylic acid functional groups and modified carboxylic acid functional groups extending therefrom. A first portion of the modified carboxylic acid functional groups are modified by a PEG oligomer having a terminal methoxy functional group and a second portion of the modified carboxylic acid functional groups are modified by a PEG oligomer having at least one terminal sulfur moiety.

14 Claims, 10 Drawing Sheets

(56) References Cited

PUBLICATIONS

Biju, Vasudevanpillai et al., Delivering quantum dots to cells: bioconjugated quantum dots for targeted and nonspecific extracellular and intracellular imaging, Chemical Society Reviews, May 27, 2010, vol. 39, pp. 3031-3056.

Zrazhevskiy, Paul et al., Designing multifunctional quantum dots for bioimaging, detection, and drug delivery, Chemical Society Reviews, Dec. 23, 2009, vol. 39, pp. 4326-4354.

Pinaud, Fabien et al., Probing cellular events, one quantum dot at a time, Nature Methods, Apr. 2010, vol. 7, No. 4, pp. 275-285.

Jaiswal, Jyoti K. et al., Long-term multiple color imaging of live cells using quantum dot bioconjugates, Nature Biotechnology, Jan. 2003, vol. 21, pp. 47-51.

Gao, Xiaohu, et al., In vivo cancer targeting and imaging with semiconductor quantum dots, Nature Biotechnology, Aug. 2004, vol. 22, No. 8, pp. 969-976.

Rossetti, R. et al., Size effects in the excited electronic states of small colloidal CdS crystallites, Journal of Chemical Physics, 1984, vol. 80, pp. 4464-4469.

Murray, C. B. et al., Synthesis and Characterization of Nearly Monodisperse CdE (E=S, Se, Te) Semiconductor Nanocrystallites, American Chemical Socity, 1993, vol. 115, pp. 8706-8715.

Dabbousi, B. O. et al., (CdSe)Zns Core-Shell Quantum Dots: Synthesis and Characterization of a Size Series of Highly Luminescent Nanocrystallites, 1997, vol. 101, pp. 9463-9475.

Liu, Wenhao et al., Compact Biocompatible Quantum Dots Functionalized for Cellular Imaging, Journal of American Chemical Society, 2008, vol. 130, pp. 1274-1284.

Susumu, Kimihiro et al., Multifunctional ligands based on dihydrolipoic acid and polyethylene glycol to promote biocompatibility of quantum dots, Nature Protocols, 2009, vol. 4, No. 3, pp. 424-436.

Jung, Jongjin et al., Selective Inhibition of Human Tumor Cells through Multifunctional Quantum-Dot-Based siRNA Delivery, Angew. Chem. Inc. Ed., 2010, vol. 49, pp. 103-107.

Liu, Wenhao et al., Compact Biocompatible Quantum Dots via RAFT-Mediated Synthesis of Imidazole-Based Random Copolymer Lignad, American Chemical Society, 2010, vol. 132, pp. 472-483.

Lee, Jae-Hyun et al., Artificially engineered magnetic nanoparticles for ultra-sensitive molecular imaging, Jan. 2007, vol. 13, No. 1, pp. 95-99.

Stewart, Michael H. et al., Multidentate Poly(ethylene glycol) Ligands Provide Colloidal Stability to Semiconductor and Metallic Nanocrystals in Extreme Conditions, Journal of American Chemical Society, 2010, vol. 132, pp. 9804-9813.

Muro, Eleonora et al., Small and Stable Sulfobetaine Zwitterionic Quantum Dots for Functional Live-Cell Imaging, Journal of American Chemical Society, 2010, vol. 132, pp. 4556-4557.

Lees, Emma E. et al., Experimental Determination of Quantum Dot Size Distributions, Ligand Packing Densities, an Bioconjugation Using Analytical Ultracentrifugation, American Chemical Society, 2008, vol. 8, No. 9, pp. 2883-2890.

Liu, Lu et al., Bifunctional Multidentate Ligand Modified Highly Stable Water-Soluble Quantum Dots, Inorganic Chemistry, American Chemical Society, 2010, vol. 49, pp. 3768-3775.

Clapp, Aaron R. et al., Capping of CdSe—ZnS quantum dots with DHLA and subsequent conjugation with proteins, Nature Protocols, 2006, vol. 1, No. 3, pp. 1258-1266.

Qu, Lianhua et al., Alternative Routes toward High Quality CdSe Nanocrystals, American Chemical Society, 2001, vol. 1, No. 6, pp. 333-337.

Mei, Bing C., Modular poly(ethylene glycol) ligands for biocompatible semiconductor and gold nanocrystals with extended pH and ionic stability, J. Mater. Chem., 2008, vol. 18, pp. 4949-4958.

Uyeda, Tetsuo H. et al., Synthesis of Compact Multidentate Ligands to Prepare Stable Hydrophilic Quantum Dot Fluorophores, Journal of American Chemical Society, 2005, vol. 127, pp. 3870-3878.

Choi, Chung Hang J., et al., Mechanism of active targeting in solid tumors with transferrin-containing gold nanoparticles, PNAS, Jan. 19, 2010, vol. 107, No. 3, 1235-1240.

Clapp, Aaron R. et al., Fluorescence Resonance Energy Transfer Between Quantum Dot Donors, Journal of American Chemical Society, 2004, vol. 126, pp. 301-310.

Medintz, Igor L., et al., Proteolytic activity monitored by fluorescence resonance energy transfer through quantumdot-peptide conjugates, Nature Materials, Jul. 2006, vol. 5, pp. 581-589.

Chen, Chun-Yen et al., Potassium ion recognition by 15-crown-5 functionalized CdSe/ZnS quantum dots in H2O, Chem. Commun, 2006, pp. 263-265.

Susumu, Kimihiro et al., Colloidal Quantum Dots: Synthesis, Photophysical Properties, and Biofunctionalization Strategies, Atrech House, Aug. 25, 2008, pp. 1-26.

Hines, Margaret A., et al., Synthesis and Characterization of Strongly Luminescing ZnS-Capped CdSe Nanocrystals, J. Phys. Chem, American Chemical Society, 1996, vol. 100, No. 2, pp. 468-471.

van Embden, Joel et al., Mapping the Optical Properties of CdSe/CdS Heterostructure Nanocrystals: The Effects of Core Size and Shell Thickness, Journal of American Chemical Society, 2009, vol. 131, pp. 14299-14309.

Gerion, Daniele, et al., Synthesis and Properties of Biocompatible Water-Soluble Silica-Coated CdSe/ZnS Semicondutor Quantum Dots, J. Phys. Chem. B, 2001, vol. 105, pp. 8861-8871.

Bhang, Suk Ho et al., Hyaluronic Acid-Quantum Dot Conjugates for In Vivo Lymphatic Vessel Imaging, American Chemical Society, May 28, 2009, vol. 3, No. 6, pp. 1389-1398.

Yildiz, Ibrahim et al., Biocompatible CdSe—ZnS Core-Shell Quantum Dots Coated with Hydrophilic Polythiols, American Chemical Society, 2009, vol. 25, No. 12, pp. 7090-7096.

Yildiz, Ibrahim et al., Biocompatible CdSe—ZnS Core-Shell Quantum Dots with Reactive Function Groups on Their Surface, Langmuir, 2010, vol. 26, No. 13, pp. 11503-11511.

Shen, Hongyan et al., Poly(ethylene glycol) Carbondiimide Coupling Reagents for the Biological and Chemical Functionalization of Water-Soluble Nanoparticles, American Chemical Society, 2009, vol. 3, No. 4, pp. 915-923.

Anderson, Robin E. et al., Systematic Investigation of Preparing Biocompatible, Single, and Small ZnS-Capped CdSe Quantum Dots with Amphiphilic Polymers, American Chemical Society, 2008, vol. 2, No. 7, pp. 1341-1352.

Bullen, C. et al., The Effects of Chemisorption on the Luminescence of CdSe Quantum Dots, Langmuir, 2006, vol. 22, pp. 3007-3013.

Munro, Andrea M. et al., Quantitative Study of the Effects of Surface Ligand Concentration on CdSe Nanocrystal Photoluminescence, J. Phys. Chem. C, 2007, vol. 111, pp. 6220-6227.

Mei, Bing C. et al., Effects of Ligand Coordination Number and Surface Curvature on the Stability of Gold Nanoparticles in Aqueous Solutions, Langmuir, American Chemical Society, 2009, vol. 25, No. 18, pp. 10604-10611.

Na, Hyon Bin et al., Multidentate Catechol-Based Polyethylene Glycol Oligomers Provide Enhanced Stability and Biocompatibility to Iron Oxide Nanoparticles, American Chemical Society, 2012, vol. 6, No. 1, pp. 389-399.

\* cited by examiner

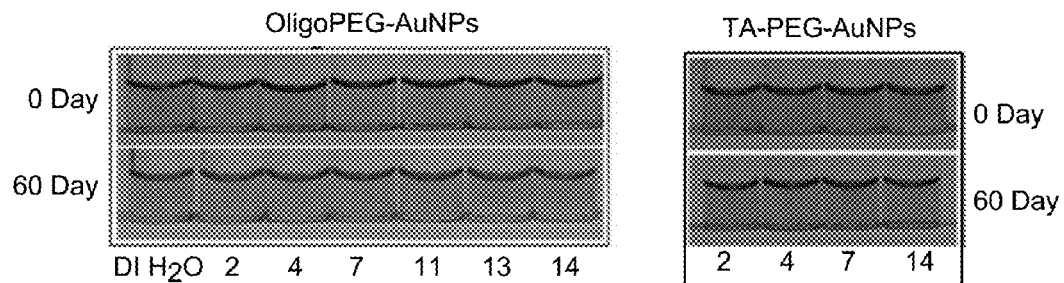
FIG. 7A
FIG. 7B
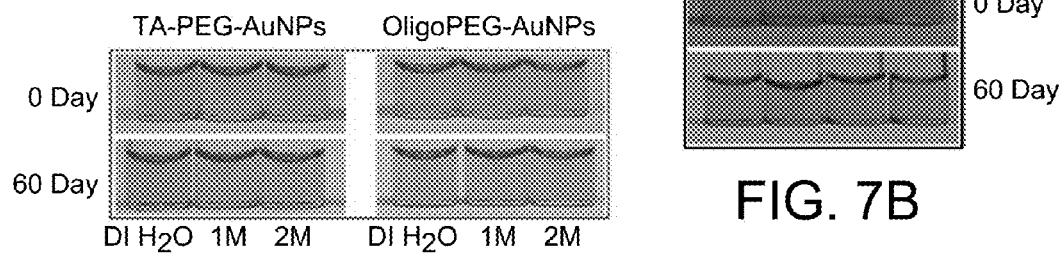
FIG. 7C
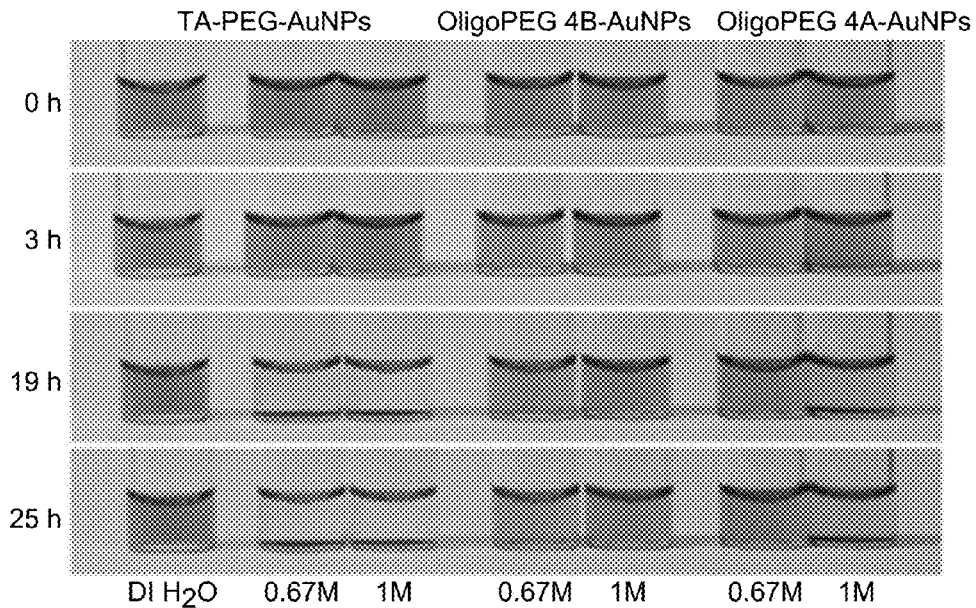
FIG. 7D

POLYETHYLENE GLYCOL BASED OLIGOMERS FOR COATING NANOPARTICLES, NANOPARTICLES COATED THEREWITH, AND RELATED METHODS

CROSS-REFERENCE TO RELATED APPLICATIONS

This application is a divisional application of U.S. application Ser. No. 13/772,595, which was filed Feb. 21, 2014 and which is incorporated herein by reference as if set forth in its entirety. U.S. application Ser. No. 13/772,595 is a continuation-in-part of U.S. application Ser. No. 13/608,119 filed Sep. 10, 2012 and titled "Multidentate Polyethylene Glycol Based Oligomers, Nanoparticles Coated Therewith, and Related Methods," and which is incorporated herein by reference as if set forth in its entirety. U.S. application Ser. No. 13/608,119 claims the benefit of U.S. Provisional Application Ser. No. 61/532,756 filed Sep. 9, 2011 and titled "Ligands for Biocompatible Nanoparticles." All of the referenced applications are incorporated by reference as if set forth in their entireties.

STATEMENT REGARDING FEDERALLY SPONSORED RESEARCH OR DEVELOPMENT

This invention was made with Government support under Grant CHE-1058957 awarded by the National Science Foundation. The Government has certain rights in the invention.

FIELD OF THE INVENTION

This invention relates to the field of nanoparticle coatings. More particularly, the invention relates to bio-compatible nanoparticle coatings.

SEQUENCE LISTING

This application contains a Sequence Listing electronically submitted via EFS-web to the United States Patent and Trademark Office as a text file named "Sequence_Listing.txt." The electronically filed Sequence Listing serves as both the paper copy required by 37 C.F.R. §1.821(c) and the computer readable file required by 37 C.F.R. §1.821(c). The information contained in the Sequence Listing is incorporated herein by reference in its entirety.

BACKGROUND

Inorganic nanoparticles such as semiconductor quantum dots (QDs) and gold nanoparticles (AuNPs) are promising materials for use in an array of applications ranging from electronic devices,[1,2] lasers,[3,4] photovoltaic cells,[5,6] analytical sensors,[7,8] and biomedical imaging.[9-13] Their promise stems from some of their unique physical and chemical properties that often exhibit size- and composition-dependence. For example, semiconductor nanocrystals such as those made of CdSe, CdS, and InAs cores have tunable size-dependent absorption, high extinction coefficients, and size-dependent Gaussian emission profiles, which are not easily obtainable with conventional organic fluorophores and fluorescent proteins;[2,9,10,13] CdSe-based nanocrystals, in particular, exhibit remarkable resistance to chemical and photo-degradation.[9,14,15] These features have generated a great interest for developing QDs as fluorescent platforms for use in biotechnology.[9-16] Such platforms promise great advances in understanding a variety of biological processes, ranging from sensing to the tracking of intracellular protein movements and interactions.

To be successfully integrated in biotechnology, however, the nanoparticles should be robust, water dispersible, and exhibit long term stability over a wide range of physiological conditions. The nanoparticles should also be compatible with bio-conjugation techniques in order to allow straightforward and controllable coupling to biomolecules such as amino acids, peptides proteins, nucleic acids, and DNAs.

Three chemical approaches have been employed to synthesize luminescent QDs: 1) growth in inverse micelles (aqueous) carried at room temperature,[17,18] 2) pyrolysis of organometallic precursors at high temperature and in coordinating solution,[19-21] and 3) arrested precipitation carried out in aqueous solution using hydrophilic ligands such as thioglycolic acid.[22,23] QDs grown at high temperature exhibit better physical characteristics; namely, a narrow size distribution, crystalline cores, and superior optical and spectroscopic properties, including high fluorescence quantum yields.[19-21,24-26]

Unfortunately, however, the QDs made using these techniques are coated with hydrophobic ligands, making them dispersible only in organic solutions. In order to render these coated QDs water dispersible and, thereby compatible with physiological conditions the coating must subsequently be modified, adding an undesirable extra step to complicate the process.

Gold nanoparticles are often prepared using the classic citrate reduction of aurate pioneered by Turkevich and Frens.[27-28] This synthetic route provides citrate-stabilized nanoparticles. Like the QDs, in order to render these gold nanoparticles water dispersible, their coatings must be modified with hydrophilic ligands if further conjugation to biomolecules is desired.

Several strategies for rendering QDs water dispersible have previously been developed. These strategies include silica coating,[29-31] encapsulation within amphiphilic polymers and lipid micelles,[32-38] and exchanging the native hydrophobic coating with hydrophilic organic ligands.[39-43] The latter strategy, called "cap exchange," is widely used because it is relatively easy to implement, and it tends to produce compact nanorcyrtals[39-42] having a small hydrodynamic size.

Regardless of the strategy used, hydrophilic nanocrystals preferably have a few key properties, including: colloidal stability over a broad range of buffers and in biological media and compatibility with easy to implement bio-conjugation techniques. The compatibility with easy to implement bio-conjugation techniques allows for specific biomolecules (e.g., peptides and proteins) to be attached to the nanocrystal surfaces to form functional platforms that can be used for developing nanoparticle-based sensing, imaging, and in vivo tracking materials.

For the cap exchange strategy, the stability of the nanocrystals is determined by the nature of the capping ligand (coating) and its affinity to the inorganic nanocrystal surface. Anchoring groups, such as thiols, histidines, and amines have been used for ligand exchange.[10,40,41,42,44-46] The overall mechanism for interaction and binding between to the nanocrystals is driven by coordination chemistry (i.e., dative not covalent binding). Among these, thiol groups exhibit stronger affinity to several metal and semiconductor surfaces. Thiol-appended ligands have been used by several groups to cap ZnS-overcoated nanocrystals (CdSe—ZnS and others).[39-42,47-49]

Studies show that CdSe—ZnS QDs capped with dihydrolopoic acid (DHLA) exhibit much better stability than those cap exchanged with monothiol appended ligands (due to the chelating effect of the bidentate anchoring group), even though long term stability is limited to basic buffer conditions.[39] QDs cap exchanged with polyethylene glycol (PEG)- and zwitterion-appended dihydrolipoic acid (DHLA) ligands exhibit enhanced stability over a broad range of biological conditions, such as high electrolyte concentration and over a wide range of pHs.[40,48,50] More recently the Michael addition technique was used to append two thioactic acid (TA), or DHLA groups onto the PEG, producing a higher coordination onto Au and QD surfaces, respectively.[47]

The bis(TA)-PEG and bis(DHLA)-PEG ligands substantially improved the stability of water dispersions of AuNPs and QDs compared to monothiol- and dithiol-terminated analogues. Nonetheless, further functionalization of those ligands with reactive groups is tedious. These finding clearly indicated that increased coordination of the ligand onto the nanocrystal surface is beneficial.

In this context, some researchers have focused on increasing the coordination to the metal surfaces by grafting a mercaptoethylamine groups onto a short polyacrylic acid (PAA) backbone. In these studies, approximately 15% of the carboxy groups along the PAA backbone were reacted with mercaptoethylamine groups. When QDs were coated with these polymers, coated QDs were dispersible in aqueous media[51] because of the availability of several carboxy groups on the nanocrystals.

Using similar concepts, other researchers designed a coating polymer made of a polymethacrylate chain appended with several lateral PEG, namely PEG2000, chains. Some of the PEG chains were terminally functionalized with TA anchoring groups. CdSe—ZnS nanoparticles coated with these coating polymers are dispersible in buffer media.[52,53]

Although these coating polymers are water dispersible, improvement is needed.

SUMMARY

We have developed nanoparticle coatings that are water dispersible, have a strong affinity for binding to gold and/or semi-conductor nanoparticles, and can be easily modified for attaching the coating to biological materials. The nanoparticle coatings comprise a polyacrylic acid based backbone onto which PEG-based oligomers are appended by modifying the native carboxyl groups of the PAA backbone. The PEG-based oligomers include functional groups on their terminal ends, which are chosen to provide a certain function. Some of the terminal functional groups bind the coatings to the nanoparticle's surface, while others provide reactive sites for binding other compounds to the coating. The method we developed for making these coatings allows one to tune the number and type of PEG-based oligomers appended to the PAA backbone based on the desired properties of the coating.

In accordance with a composition aspect of the invention, the nanoparticle coatings comprise repeating polyacrylic acid monomers covalently bound together in an aliphatic chain having a plurality of carboxylic acid functional groups and modified carboxylic acid functional groups extending therefrom. A first portion of the modified carboxylic acid functional groups are modified by a PEG oligomer having a terminal methoxy functional group and a second portion of the modified carboxylic acid functional groups are modified by a PEG oligomer having at least one terminal sulfur moiety.

These and other aspects, embodiments, and features of the invention will be better understood in the context of the accompanying drawings and the following Detailed Description of Preferred Embodiments.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 4A and 4B show FT-IR spectra of: (FIG. 4A) TOPO ligand only (black, broken line), TOP/TOPO-capped QDs in toluene (black, solid line), Compound 5B pure (red, broken line), and OligoPEG-capped QDs in water (red, solid line) after ligand exchange. The top arrows refer to the peaks ascribed to CH stretching (at ~2917, 2849 cm$^{-1}$) and P=O stretching (at ~1144 cm$^{-1}$) of TOP, whereas the bottom arrows designate the new peaks ascribed to the amide band of the OligoPEG (at ~1648 cm$^{-1}$ and ~1546 cm$^{-1}$). (FIG. 4B) Tribasic citrate ligand only (black, broken line), citrate-stabilized AuNPs (black, solid line), Compound 4B pure (red, broken line) and OligoPEG-capped AuNPs in water (red, solid line). The top arrow designates to the COOH band of the citrate, while the bottom ones designate the amide bands as provided in (a).

FIG. 7A shows optical images of AuNPs (10 nm) capped with Compound 4B (OligoPEG-TA) in phosphate buffer at different pH values; each vial contains 3 nM AuNPs.

FIG. 7B shows side-by-side optical images of AuNPs stabilized with TA-PEG-OCH$_3$ and OligoPEG-TA (Compound 4B) at three pHs (2, 4, 7 and 14).

FIG. 7C shows optical images of AuNPs stabilized with TA-PEG-OCH$_3$ and Compound 4B in the presence of 1M and 2M NaCl.

FIG. 7D shows optical images of AuNPs (10 nm) capped with TA-PEG-OCH$_3$, Compound 4A and 4B in the presence of 0.67M and 0.1M DTT, and 0.4M NaCl, both were tracked over 25 hours.

DETAILED DESCRIPTION OF PREFERRED EMBODIMENTS

In the Summary above and in the Detailed Description of Preferred Embodiments, reference is made to particular features (including method steps) of the invention. Where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other features, ingredients, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

This invention may be embodied in many different forms and should not be construed as limited to the embodiments set forth herein. Rather, these embodiments are provided so that this disclosure will convey preferred embodiments of the invention to those skilled in the art.

We have developed new set of PEG-based oligomer nanoparticle coating ligands that have increased coordination to metal and semiconducting nanocrystal surfaces, affinity to aqueous media, and the ability to be conjugated to bio-molecules. For this, the inventors have used PAA as a central backbone onto which PEG-based oligomers are bound using a simple approach based on N,N-dicyclohexylcarbodiimide DCC coupling. These PEG-based oligomers can be used for coating metallic nanoparticles. Reduced derivatives of these PEG-based oligomers can be used for coating semiconductor nanoparticles such as QDs.

The process for making these PEG-based oligomer coatings, also developed by the inventors, allows specific functional groups such as azides and amines to be incorporated into the coating. These PEG-based oligomer coatings exhibit one or more of the following advantageous features: (i) they include multiple nanoparticle anchoring groups bound to a single PAA oligomer, (ii) they include multiple PEG oligomers bound to a single PAA oligomer, and (iii) the number of reactive functional groups incorporated into the coating is tunable.

Cap exchange with these ligands provides QDs and AuNPs that exhibit remarkable stability to pH changes, to added excess of electrolyte, and that are compatible with simple conjugation strategies to bio-molecules. We also found that much smaller amounts of excess ligands than those used for DHLA-PEG, for example, are required. Further, using these PEG-based oligomer coatings, cap exchange of QDs may be carried out at room temperature.

Figure 1:
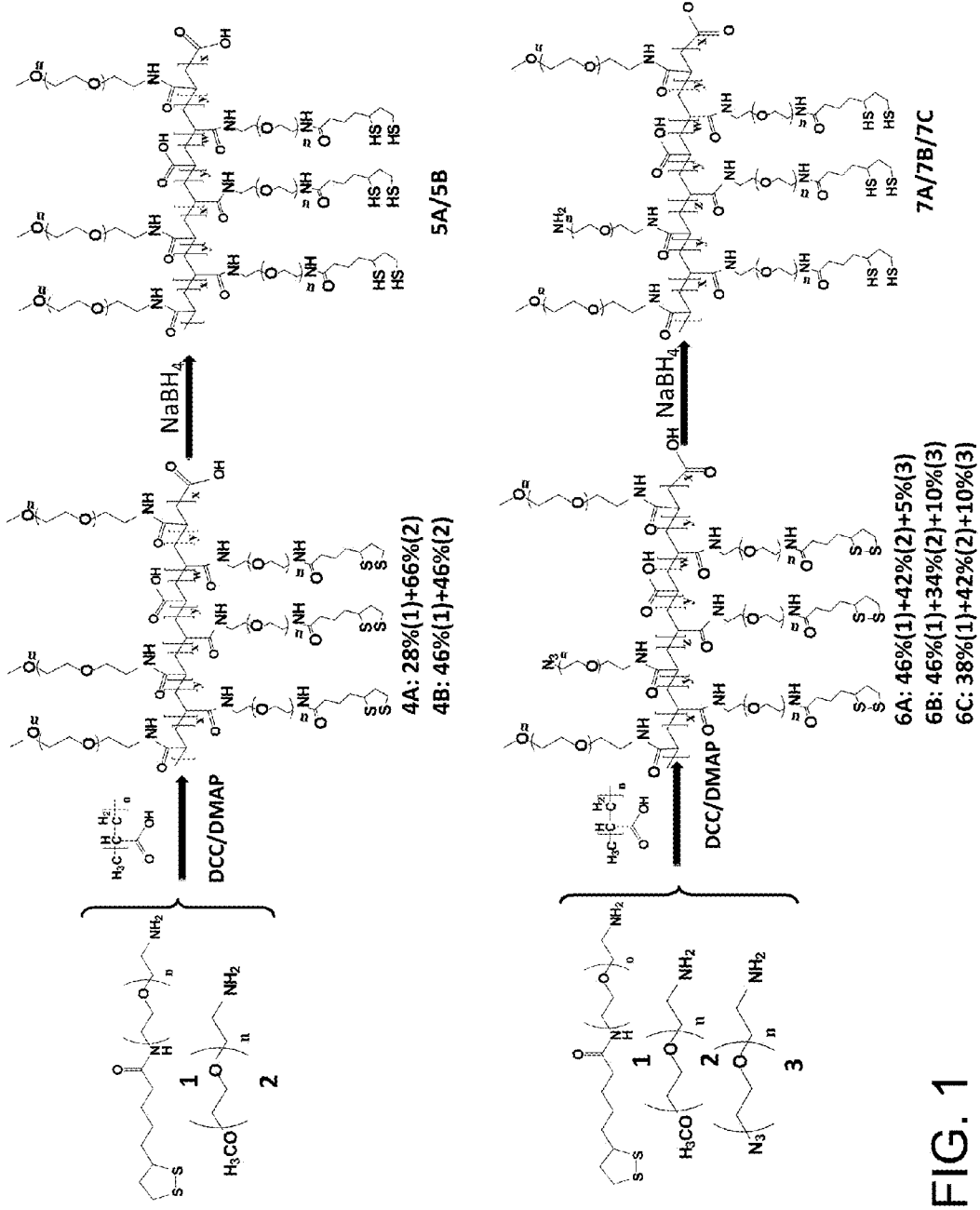
FIG. 1 is a schematic diagram of the chemical structures and synthetic strategy of making nanoparticle coatings in accordance with an embodiment of the invention where x, y, z, and w designate the relative abundance of methoxy-PEG, TA/DHLA-PEG, $N_3/NH_2$-PEG, and unreacted carboxyl along the PAA chain

A first composition aspect of the invention is now described with reference to FIG. 1. In FIG. 1, several of the preferred PEG oligomers and nanoparticle coatings are shown. For ease of reference, each is assigned a corresponding compound number, which appears below the compound's molecular diagram. The abbreviations used are summarized in Table 1.

In a preferred embodiment of the first composition aspect of the invention, the PEG-based nanoparticle coating is composed of repeating polyacrylic acid monomer units covalently bound together to form an aliphatic chain having a plurality of carboxylic acid functional groups and modified carboxylic acid functional groups extending therefrom. The number of polyacrylic acid monomer units is preferably between about 20 to about 30. More preferably, the number of polyacrylic acid monomer units is about 25.

The modified carboxylic acid functional groups are formed by modifying a portion of the native carboxylic acid groups on the polyacrylic acid monomer units. Preferably, the modified carboxylic acid functional groups include amide groups formed from the combination of the aliphatic PAA chain with aminated PEG-based oligomers.

A first portion of the modified carboxylic acid functional groups are modified by a PEG oligomer having a terminal methoxy functional group such as Compound 2. A preferred average molecular weight for the PEG section of Compound 2 is about 750 (PEG 750). The terminal methoxy functional groups are preferred because they are generally not reactive with the surface of nanoparticles or bio-molecules.

A second portion of the modified carboxylic acid functional groups are modified by a PEG oligomer having at least one terminal sulfur moiety. Because the terminal sulfur moiety(ies) bond to the surface of many nanoparticles, they are effective at anchoring the nanoparticle coating to the surface of a nanoparticle. Preferred terminal sulfur moieties are formed from sulfur moieties including, but not limited to thioactic acid and dihydrolipoic acid.

In a particular embodiment, the PEG oligomer having at least one terminal sulfur moiety is formed from Compound 1. A preferred molecular weight of the PEG section of Compound 1 is about 600 (PEG 600).

In another particular embodiment, the PEG oligomer having at least one terminal sulfur moiety is formed from dihydrolipoic acid, which is a reduced derivative of thioctic acid.

Optionally, a third portion of the modified carboxylic acid functional groups are modified by a PEG oligomer having a terminal azide functional group. A preferred PEG oligomer having a terminal azide functional group is formed from Compound 3.

Alternatively, the third portion of the modified carboxylic acid functional groups are modified by a PEG oligomer having a terminal amine functional group. The terminal amine function group is preferably formed by reducing the terminal azide group.

In a second composition aspect of the invention, nanoparticles are coated with one or more of the nanoparticle coatings described above. The nanoparticles are preferably selected from metallic nanoparticles, semiconductor nanoparticles, or a combination thereof. Examples of preferred metallic nanoparticles include gold or other metal-based nanoparticles to which sulfur-containing ligands will bind. Examples of preferred semiconductor nanoparticles include CdSe nanoparticles, ZnS, CdSe—ZnS nanoparticles or other semiconductor-based nanoparticles to which sulfur-containing ligands will bind. In these preferred examples, the nanoparticles are coated by being directly bound to the at least one terminal sulfur moiety.

A preferred method of making multidentate polyethylene glycol (PEG)-based oligomer nanoparticle coatings, in accordance with a method aspect of the invention, is now described. The method is initiated by cooling a first solution of PAA and a solvent to a first temperature. Preferably, the first temperature is approximately −5° C. to approximately 5° C., or, more preferably, about 0° C. The solvent is preferably a polar aprotic organic solvent such as DMF or the like. DCC is then blended with the first solution at approximately the first temperature to form a second solution. The temperature of the second solution is subsequently elevated to a second temperature, which is preferably approximately 75° C. to approximately 85° C., or, even more preferably, approximately 80° C. Compound 1 and compound 2 from FIG. 1, along with DMAP are mixed with the second solution to form a third solution comprising the nanoparticle coating.

If thioctic is used to provide the terminal sulfur moieties, the nanoparticle coatings that result from this method may be further treated to convert terminal disulfide moieties on thioctic into terminal thiol groups, which help the coatings bind to the surface of semiconductor nanoparticles. Accordingly, if the nanoparticle coatings are intended to coat semi-conductor nanoparticles, it may be desirable to reduce thioctic acid groups on the nanoparticle coating to dihydrolipoic acid groups by adding $NaBH_4$ to a solution of the nanoparticle coating. This is achieved while maintaining a pH of the solution of the nanoparticle coating at approximately 6 to approximately 7.

If desired, a PEG oligomer having a terminal azide functional group, such as compound 3, may be added during the mixing step to facilitate binding the nanoparticle coating to biological material via azide-alkyne cycloaddition chemistry. The azide groups of the azide functionalized nanoparticle coatings may then be reduced to amine groups using $NaBH_4$.

A particularly advantageous feature of this method is the fact that the number of terminal sulfur moieties and terminal methoxy groups attached along the PAA chain can be engineered as desired by changing the amount of TA-PEG-$NH_2$ relative to the number of carboxyl groups along the native PAA chain in the synthesis process.

In FIG. 1, Compounds 4A and 4B differ by the number of TA-PEG-NH— and $H_3$CO-PEG-NH— groups. For Compound 4A, about 28% of the carboxyl groups on the native PAA chain were modified with TA-PEG-NH— groups and about 66% of the carboxyl groups on the native PAA chain were modified with $H_3$CO-PEG-NH—. Compounds 5A and B contain the same relative percentages, except that the terminal TA groups are reduced to DHLA groups.

Similarly, Compounds 6A, 6B, and 6C differ by the number of TA-PEG-NH— groups, $H_3$CO-PEG-NH— groups, and N3-PEG-NH— groups. For compound 6A, about 46% of the carboxyl groups on the native PAA chain were modified with TA-PEG-NH— groups, about 42% of the carboxyl groups on the native PAA chain were modified with $H_3$CO-PEG-NH—, and about 5% of the carboxyl groups on the native PAA chain were modified with N3-PEG-NH— groups. Compounds 6B and 6C differ by the % shown.

EXAMPLES

The embodiments of the invention described above will be even better understood in the context of the following examples. These examples are not intended to limit the scope of the invention in any way.

The examples below show that we have provided an advantageous synthetic strategy for developing a set of multifunctional, multidentate PEGylated oligomer (OligoPEG) ligands (nanoparticle coatings) with tunable numbers of metal-coordinating sulfur moieties and reactive groups. The synthesis scheme relied on DCC/DMAP coupling and allowed grafting of a controllable number of surface-coordinating, or end-reactive, PEGylated moieties along a short poly acrylic acid (PAA) backbone. We showed that these OligoPEG ligands can easily promote the transfer of luminescent QDs and Au nanocrystals alike to buffer media, with excellent long term stability of both set of nanocrystals over a broad range of pHs and in the presence of added excess electrolytes. Furthermore, the ability to introduce different functional groups (such as $N_3$ and $NH_2$) into the oligomers opens the opportunity for orthogonal coupling of these nanoparticles to target biomolecules such as proteins and peptides, providing biologically active particle-platforms for use in imaging and sensing.

The results clearly confirm that higher ligand affinity to the nanoparticle surfaces (via increased sulfur coordination number) produces substantial enhancement in colloidal stability for AuNPs and CdSe—ZnS QDs alike. Our design combines tunable multi-coordination, hydrophilicity, reduced non specific interactions via adjustable PEG moieties and reactivity, all in the same oligomer.[35,41,59] These observations open up a whole range of opportunities to couple different biological molecules with specific properties and functions to QDs and AuNPs and use them as platforms for sensing and imaging.

It is important to note that these coatings also permit the dispersion of these nanocrystals in several polar organic solvents such methanol and ethanol. Moreover, this design can be easily extended to assemble custom-designed OligoPEG ligands with selective affinity to other homogeneous or hybrid inorganic nanocrystals such as those exhibiting magnetic properties. For example, we have recently prepared characterized and used dopamine appended PEGylated oligomers and used them for cap exchanging iron oxide nanoparticles and promote their transfer to buffer media.[67]

Example 1

PEG-Based Coatings for Metallic and Semiconductor Nanoparticles

1. Synthesis and Design: PEG-Modification of Polyacrylic Acid

The nanoparticle coatings we developed for the stabilization of metallic and semiconductor nanoparticles were synthesized by laterally grafting one or a combination of TA-PEG600-$NH_2$, $H_3$CO-PEG750-$NH_2$ and $N_3$-PEG600-

NH₂ moieties on a commercially available short chain PAA. These molecular scale ligands were prepared using synthetic schemes described in previous reports.[40,42] Grafting of aminated-PEG moieties (Compound 1, Compound 2, and/or Compound 3 shown in FIG. 1) onto the PAA backbone relied on dicyclohexylcarbodiimide (DCC) mediated reaction between amine and carboxy groups, in the presence of a catalytic amount of 4-dimethylamino-pyridine (DMAP); the list of prepared compounds is provided in Table 2. The grafted PEG moieties present a combination of anchoring groups for tight binding to the nanoparticle surfaces and a mixture of azide and methoxy terminal groups. The methoxy groups are used to control the fraction of reactive groups, which can be used for further modification and coupling to target molecules.

Synthesis of Methoxy OligoPEG-TA (Compounds 4A and 4B).

Compounds 4A and 4B have similar structure, except that 4A has a slightly lower grafting fraction of TA-PEG moieties. For 4A we used a nominal ratio of TA-PEG-NH₂ to COOH (on the PAA) of 30%, whereas for 4B that ratio was increased to ~50%. We detail the synthesis of 4B.

Polyacrylic acid (PAA) (1.0 g~0.56 mmol) and 50 mL of dimethylformamide (DMF) were placed in a 250 mL round-bottom flask and the mixture was cooled to ~0° C. DCC (2.9 g, 14.0 mmol) was added under ice-cold conditions, and the mixture was stirred for ~30 min, followed by heating to ~85° C. When the temperature of the mixture was equilibrated, a solution containing TA-PEG600-NH₂ (5.5 g, 7.0 mmol) and H₂N-PEG750-OCH₃ (5.3 g, 7.0 mmol) in DMF (30 mL) was added slowly, followed by DMAP (225 mg, 1.9 mmol), and the reaction mixture was left stirring for four days under nitrogen atmosphere before removing the dicyclo-urea (DCU) side-product by filtration. DMF was removed under vacuum, then 100 mL of distilled water was added to the residue and this mixture was washed with diethyl ether (100 mL, two times) to remove residual DCU, followed by washing with ethyl acetate (100 mL, two times).[54] The mixture was lyophilized to remove the water and the crude product was dissolved in CHCl₃. The solution containing the crude product was filtered to remove unreacted PAA, slightly dried and then chromatographed on a silica column (230-400 mesh) using a mixture of chloroform-methanol (20:1) as the eluent; this procedure yielded compound 4B as a viscous dark yellow liquid (7.0 g, ~65% yield).

$^1$H NMR (600 MHz, CDCl₃) for compound 4A: δ 6.41 (br, s), 3.77-3.57 (m), 3.58-3.54 (m, 96H,), 3.48-3.40 (m, 22H), 3.37 (s, 49.82H), 3.2-3.14 (m), 3.13-3.07 (m), 2.48-2.40 (m, 8H), 2.41-2.22 (br, 25H), 2.18 (t, J=7.8 Hz, 14H), 1.93-1.85 (m), 1.84-1.73 (br), 1.72-1.04 (m). IR (neat): 3327.5, 2870, 1655.6, 1544.4, 1348.5, 1289.2, 1250.4, 1097.9, 948 cm⁻¹.

$^1$H NMR (600 MHz, CDCl₃) for compound 4B: δ 6.36 (br s,), 3.77-3.56 (m), 3.55-3.52 (m, 46H,), 3.48-3.42 (m, 15H), 3.36 (s, 34.95H), 3.2-3.16 (m), 3.12-3.07 (m), 2.48-2.40 (m, 8H), 2.41-2.22 (br, 25H), 2.18 (t, J=7.2 Hz, 22.22H), 1.91-1.87 (m), 1.86-1.75 (br,), 1.74-1.01 (m). IR (neat): 3335.8, 2866.6, 1652, 1540.2, 1452.6, 1348.9, 1290.5, 1251.6, 1094.6, 947 cm⁻¹.

Synthesis of Methoxy-OligoPEG-DHLA (Compound 5B) by Reduction of the Dithiolane Rings.

A solution of compound 4B (3.5 g.~0.18 mmol) dispersed in methanol-water mixture (2:1, v/v, 24 mL) was cooled in an ice-bath, and NaBH₄ (760 mg~2.0 mmol) dissolved in water (2 mL) was added drop wise with vigorous stirring. The reaction mixture was then left stirring for 10 hours at room temperature. 1 N hydrochloric acid was added drop wise until the pH of the solution reached ~6-7. Methanol was evaporated under vacuum and the aqueous layer was lyophilized to remove water. Chloroform was added to dissolve the compound followed by removal of salts by filtration. The solution was dried over Na₂SO₄, filtered and solvent evaporated to obtain compound 5B as colorless viscous liquid (2.0 g, yield ~58%). A similar procedure was used to prepare compound 5A by reduction of compound 4A.

$^1$H NMR of compound 5A (600 MHz, CDCl₃): δ 6.4 (br s,), 3.73-3.60 (m), 3.59-3.55 (m, 77H), 3.49-3.44 (m, 18H), 3.37 (s, 46H), 2.97-2.91 (m), 2.78-2.65 (m), 2.37-2.24 (br, 25H), 2.21 (t, J=7.2 Hz, 15H), 1.96-1.89 (m), 1.80-1.49 (m), 1.49-1.30 (m), 1.27-1.24 (m). IR (neat): 3319.8, 2870, 1655.3, 1649.9, 1538.2, 1455.7, 1360, 1335.9, 1222, 1048, 933.6 cm⁻¹

$^1$H NMR of compound 5B (600 MHz, CDCl₃): δ 6.35 (br s,), 3.74-3.60 (m), 3.57-3.51 (m, 77H,), 3.51-3.46 (t, J=5.5 Hz, 12H), 3.47-3.42 (m, 22H), 3.38 (s, 34.54H), 2.95-2.89 (m), 2.77-2.64 (m), 2.62-2.47 (br, 25H), 2.19 (t, J=8.0 Hz, 21.81H), 1.97-1.30 (m), 1.26-1.20 (m). IR (neat): 3323.8, 2866.6, 1648, 1646.7, 1452.6, 1348.9, 1297, 1248.3, 1096, 947.5 cm⁻¹.

Synthesis of Azide-functionalized OligoPEG-TA, Compounds (6A, 6B, and 6C).

To synthesize compound 6A, polyacrylic acid (1.0 g.~0.56 mmol) and DCC (2.9 g, 14.0 mmol) were dissolved in DMF (50 mL) in a 250 mL round bottom flask and stirred for 30 min under ice-cold conditions. A solution of DMF (30 mL) containing TA-PEG600-NH₂ (5.5 g, 7.0 mmol), N₃-PEG600-NH₂ (0.45 g, 0.7 mmol) and H₂N-PEG750-OCH₃ (4.72 g, 6.3 mmol) was added to the flask, and the reaction mixture was heated to ~85° C. followed by the addition of DMAP (225 mg, 1.9 mmol). After 4 days stirring at ~85° C., DCU was removed by filtration and DMF was removed under vacuum. Then 50 mL of distilled water was added to the residue and the aqueous layer was first washed with diethyl ether (100 mL, one time), then with ethyl acetate (100 mL, two times). The solution was lyophilized and the residue was re-dissolved in chloroform and filtered to remove the precipitate if any. The solvent was evaporated and the residue chromatographed on silica gel using chloroform-methanol (15:1) mixture as the eluent, to isolate compound 6A (6.5 g, yield ~62%) as a yellow gel; in compound 6A we anticipate that ~5% of the total monomer units are grafted with azide-PEG.

Using this reaction route it is possible to vary the relative fraction of the PEG moieties inserted along the PAA backbone. For instance, we prepared two additional compounds 6B and 6C where either the relative fractions of azide to methoxy groups or methoxy to TA were varied (see Table 2). For compound 6B we used N₃-PEG600-NH₂ (0.87 g, 1.4 mmol), H₂N-PEG750-OCH₃ (4.2 g, 5.6 mmol) while maintaining the amount of TA-PEG600-NH₂ (5.5 g, 7.0 mmol). We expected this to provide a ligand that has ~10% of the total grafted PEG moieties presenting terminal azides. For compound 6C, a different stoichiometry oligomer was expected, with TA-PEG (~36-40%) and PEG-OCH₃ (~40-44%) while PEG-N₃ is ~10%.

$^1$H NMR (600 MHz, CDCl₃) of compound 6A: δ 6.22 (br s), 3.76-3.56 (m), 3.54-3.52 (m, 67H), 3.44-3.41 (m, 26H), 3.39-3.37 (t, J=2.8 Hz, 2.6H), 3.36 (s, 30.94H), 3.18-3.14 (m), 3.12-3.07 (m), 2.48-2.42 (m, 11.9H), 2.41-2.22 (br, 25H), 2.18 (t, J=7.6 Hz, 22.21H), 1.92-1.86 (m), 1.8-1.73 (br), 1.73-1.04 (m). IR (neat): 3330.3, 3008.6, 2872.7, 2107.3, 1663.6, 1544.4, 1452.8, 1350.2, 1293.5, 1452.8, 1350.2, 1293.5, 1250.4, 1092.3, 950.9 cm⁻¹.

Synthesis of Amine-OligoPEG-DHLA (Compound 7A).

A solution of compound 6A (3.4 g, ~0.17 mmol) in methanol-water (2:1, v/v, 24 mL) was cooled in an ice-bath, and NaBH$_4$ (850 mg, ~2.3 mmol) dissolved in water (2 mL) was added drop wise under N$_2$ atmosphere with stirring. Once addition is complete, the reaction mixture was allowed to stir for 10 hours at ambient temperature, and 1 N hydrochloric acid was added drop wise until the pH of the solution reached ~6.5. Methanol was evaporated under vacuum at ~35-40° C., and then the aqueous layer was lyophilized to remove water. The compound was dissolved in chloroform and residual salts were removed by filtration. The organic solution was dried over Na$_2$SO$_4$, filtered and evaporated to obtain the product as colorless viscous liquid at room temperature (2.1 g, yield ~62%).

$^1$H NMR (600 MHz, CDCl$_3$) of compound 7A: δ 6.3 (br, s), 3.74-3.56 (m), 3.57-3.52 (m, 71.2H,), 3.46-3.41 (m, 25.1H), 3.36 (s, 30.9H), 3.19 (br), 2.94-2.89 (m), 2.77-2.63 (m), 2.63-2.48 (br, 25H), 2.18 (t, J=7.6 Hz, 21.75H), 1.97-1.3 (m), 1.23 (m). IR (neat): 3323.8, 2866.6, 1650, 1546.7, 1455.9, 1348.5, 1300.2, 1245, 1092.8, 950 cm$^{-1}$.

Reduction of compound 6B (to provide 7B) followed the same procedure described above for 6A, starting with 3.38 g of OligoPEG-TA (6B), though a slightly higher amount of NaBH$_4$ (900 mg, ~2.4 mmol) was used. The procedure yielded compound 7B as colorless liquid at room temperature (1.9 g, yield ~50%). $^1$H NMR peak location and assignments are identical to above (7B). IR (neat): 3328, 2868, 1662.8, 1543.6, 1455, 1386.2, 1349.6, 1291.5, 1248, 1094.7, 947.8 cm$^{-1}$.

FIG. 1 shows a schematic representation of the synthetic procedure, the steps involved, and the structure of the multifunctional oligomers prepared. Our scheme used a series of PEG moieties with the desired chain length and functional/reactive groups. TA-PEG-NH$_2$ and N$_3$-PEG-NH$_2$ (PEG Mw ~600) and H$_3$CO-PEG-NH$_2$ (Mw of PEG ~750) were first prepared according to our previous method.[40,42,57] The OligoPEG ligand synthesis used N, N-dicyclohexyl carbodiimide (DCC) condensation, to react amines on the PEG moieties with carboxylic acids on the PAA. This allowed the simultaneous incorporation of anchoring, hydrophilic and reactive groups/moieties into the same oligomer structure. Proper balance between the TAs and PEG moieties is essential to render the nanoparticles cap-exchanged with these ligands dispersible in buffer media. Here oligomers with ~7 to 12 TA-PEG moieties (or 28 to 48% of the total monomer units on the PAA) were prepared and tested. The as-prepared TA-modified OligoPEG ligands interact with AuNPs, while subsequent reduction of the dithiolane rings in the presence of sodium borohydride (NaBH$_4$) provides OligoPEG-DHLA, which can be used to transfer TOP/TOPO-capped QDs to buffer media. Furthermore, this strategy allowed us to introduce N$_3$ or NH$_2$ (obtained via reduction of N$_3$) functionalities in the final ligands; these can be used for orthogonal coupling to biological molecules.

We note that balance between the number of TAs and PEGylated moieties grafted along the PAA backbone is important. For instance, we found that grafting higher fraction of TA-PEG moieties (e.g., on more than ~50% of the total monomers) can produce hydrophobic oligomers, presumably attributed to sulfur-sulfur bridging. We found that adding a strong reducing agent such as NaBH$_4$ renders such as materials soluble in water solutions. Here, we focused on OligoPEG containing ~11-12 or smaller numbers of TA-PEG moieties.

2. Characterization of Coatings

Figure 2:
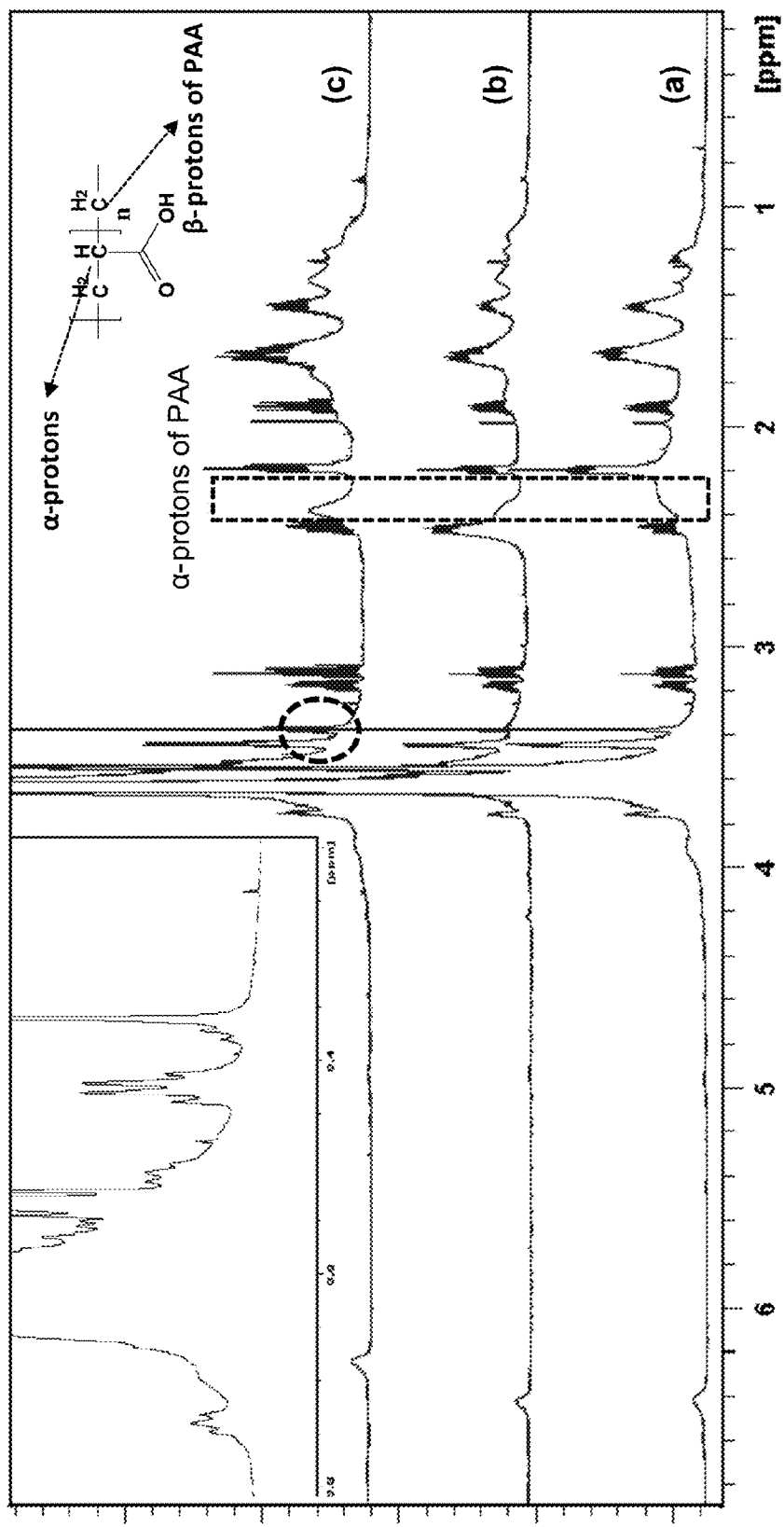
FIG. 2 shows $^1$H NMR spectra of OligoPEG ligands in CDCl$_3$: (a) compound 4A, (b) compound 4B, (c) compound 6A; inset: expansion of spectra of compound 6A showing the small peak ascribed to $N_3$ near 3.36 ppm; Integration: compound 4A ($\delta$3.36, s, 49.82H; $\delta$2.41-2.22, br, 25H; $\delta$2.18, t, 14H), compound 4B ($\delta$3.36, s, 34.95H; $\delta$ 2.41-2.22, br, 25H; $\delta$2.18, t, 22.22H), compound 6A ($\delta$3.36, s, 30.94H; $\delta$2.41-2.22, br, 25H; $\delta$2.18, t, 22.21H).

Characterization of the coatings relied on $^1$H NMR and FT-IR measurements. FIG. 2 shows $^1$H NMR spectra of three representative TA-appended OligoPEG coatings prepared in this study (namely, compounds 4A, 4B, and 6A). The data show that each spectrum combines the individual signatures of the PEG (PEG600, PEG750) chains, the polyacrylic acid backbone, and the thioctic acid groups. The PEG chains produce a large peak around 3.8-3.6 ppm, while the sharp peak at ~3.36 ppm is ascribed to the OCH$_3$ groups. The CH$_2$ repeating groups in the TA produce a broad contribution (multiple peaks spanning the range of 3.5-1.4 ppm) that partially overlaps with the β-protons of PAA. A contribution from these β-protons appears as a broad peak at 1.9-1.2 ppm, while that from the thioctic acid protons is at 1.89, 1.66, and 1.44 ppm. The broad peak at ~2.4-2.2 ppm is characteristic of the α-hydrogens (n ~25) of PAA. This peak is rather important, as it provides the integration (25 protons) used to calculate the number of PEG moieties grafted onto the PAA chain. The approximate number of TA groups per chain (i.e. grafting percentage) was determined on the basis of comparing the peak area obtained from —CH groups (α-hydrogens) of PAA at ~2.4-2.2 ppm with that from the —CH$_2$ groups of TA at 2.1 ppm (t, 2H). Conversely, the number of methoxy-PEG segments was extracted from the sharp singlet peak at ~3.36 ppm (ascribed to OCH$_3$ groups); this peak was used as reference with respect to α-hydrogens of PAA.

Analysis of the integration peaks of the spectrum shown in FIG. 2 for compound 4A and 4B provided estimates for the percentage of the overall grafting along the PAA backbone. For this, we measured the following ligand stoichiometry: 4A: TA-PEG (~28% or ~7.0 TAs), PEG-OCH$_3$ (~64-68% or ~16-17 OCH$_3$ groups); 4B: TA-PEG (44-48% or ~11-12 TAs), PEG-OCH$_3$ (at 44-48% or ~11-12 OCH$_3$ groups). For 6A, we measured ~11-12 TA-PEG (44-48%) and 10-11H$_3$CO-PEG (~40-44%) and ~1-2 (~4-8%) azides, while for 6B we estimated ~11-12 TA-PEG (44-48%) and 8-9 PEG-OCH$_3$ (~32-36%) and 2-3 (~8-12%) azides. The azide fractions were calculated using the integration for the small shoulder peak at 3.4 ppm, next to the methoxy peak at 3.36 ppm (see FIG. 2).

Overall, the $^1$H NMR data provide a good and fairly accurate account for the composition of the ligands we prepared, with estimates of the relative fractions of the different end-functionalized PEG moieties grafted along the PAA backbone. For instance, compounds 6A and 6B were prepared starting with the exact same molar amounts of TA-PEG, and the measured numbers of grafted TA groups were essentially identical. Nonetheless, such analysis also indicates that slightly lower than the optimal (100%) coupling to the carboxyl groups on the PAA took place, which may be attributed to the nature of the DCC reaction used; ~2 COOH groups were left unreacted in the final OligoPEG. FT-IR data also confirmed that a small fraction of the carboxyl groups stayed intact.

Figure 3:
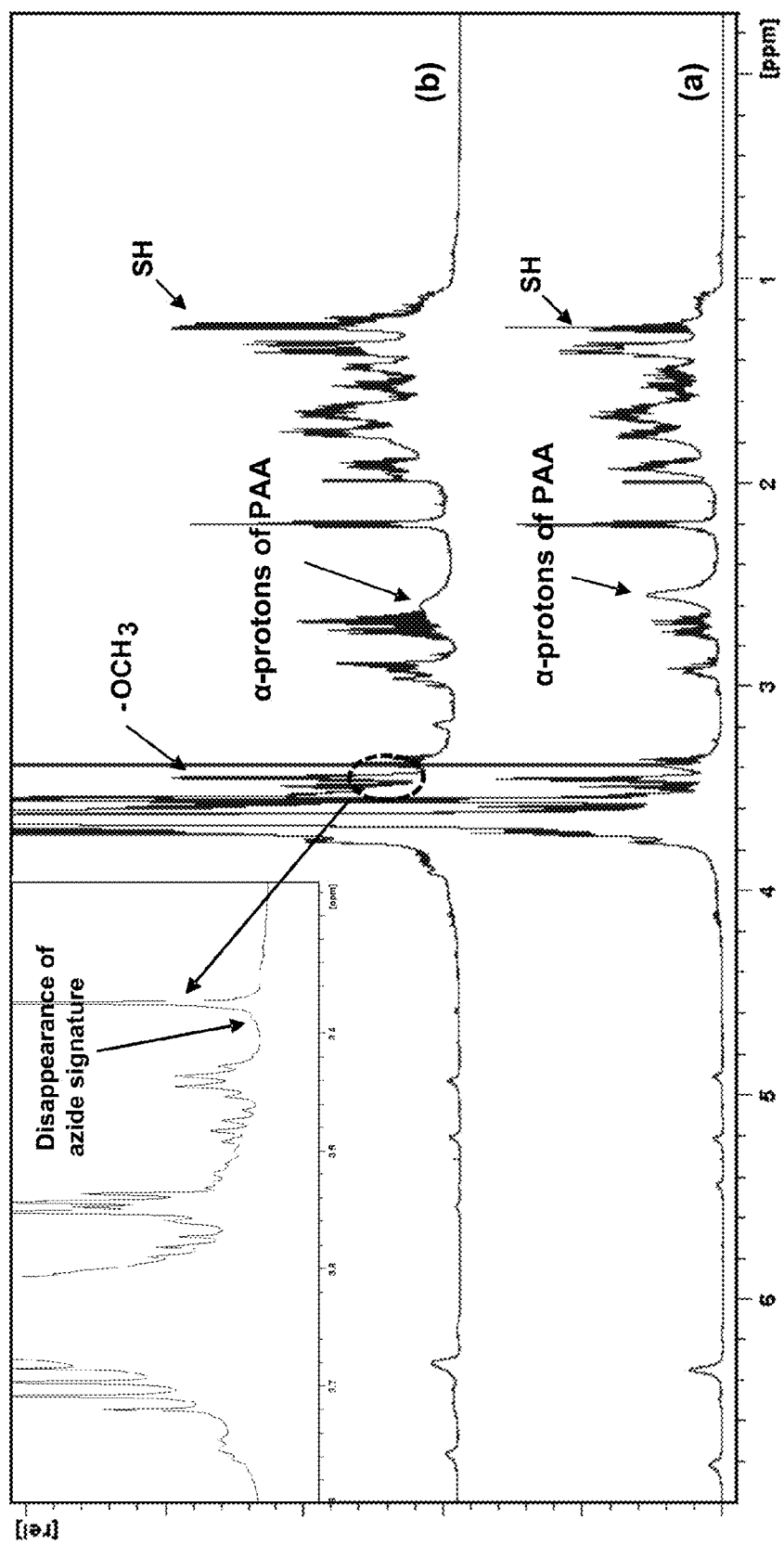
FIG. 3 shows $^1$H NMR spectra of reduced OligoPEG ligands in CDCl$_3$: (a) compound 5B, (b) compound 7A. The inset shows an expansion of the spectra around 3.3-3.7 ppm; the peak due to CH$_2$ attached to the N$_3$ group has indeed vanished after borohydride reduction.

FIG. 3 shows two representative $^1$H NMR spectra of compounds 5B and 7A, obtained after the borohydride reduction of 4B and 6A, respectively. The peaks at ~3.1 and 2.4 ppm shifted to ~2.8 and 2.7 ppm, respectively, while a new triplet peak characteristic of the —SH protons appeared at ~1.2-1.3 ppm. This clearly indicates that the borohydride reduction of the TA groups was unaffected by coupling onto the PAA and it did not alter the structure of OligoPEG ligands. Nonetheless, we found that the peak at ~3.4 ppm (indicative of azide signature) disappeared; this indicates that a transformation of the azide groups to amines has taken place, as is often the case for free TA-PEG-N$_3$ molecules in the presence of NaBH$_4$. FT-IR data confirm this transformation, as the peak at ~2100 cm$^{-1}$ disappeared from the spectrum after borohydride reduction.

We should emphasize that the present design presents a clear advantage as one can simultaneously vary the number of sulfur moieties ligands to control the binding efficiency, and the number of reactive groups on the OligoPEG according to specific requirements. If combined with modification of the nature of the reactive groups, this will allow further flexibility and control over the biological coupling and targeting of the nanocrystals.

3. Cap Exchange and Nanoparticle Functionality

Ligand exchange of both gold nanoparticles and QDs was performed using our new nanoparticle coatings. The OligoPEG-TA coating can be used to cap AuNPs. However, borohydride (NaBH$_4$) reduction of the 1,2-dithiolane groups (to DHLAs) was advantageous for performing ligand exchange with CdSe—ZnS QDs.

We used two sets of citrate-stabilized AuNPs having 10 and 15 nm diameters, and three samples of TOP/TOPO-capped QDs emitting at $\lambda_{em}$=543, 575 and 617 nm. We found that cap exchange of AuNPs with OligoPEG-TA and QDs with OligoPEG-DHLA could be carried out using smaller amounts of ligands than what is routinely used with their molecular counterparts (TA/DHLA-PEG series).[40,57] Essentially, the amount of OligoPEG ligands needed for cap exchange was about one half of that of TA- or DHLA-PEG ligands. Similarly, we found that cap exchange of QDs could be performed at lower (even room) temperature. For a typical QD cap exchange, 3 mL of growth solution (~9.0 µM) in a mixture of hexane and toluene were first precipitated using ethanol, centrifuged, and the supernatant discarded yielding a wet pellet of QDs. To this pellet OligoPEG-DHLA (5B, ~700 mg) or DHLA-PEG (~1.5 g) ligands dissolved in 0.5-1 mL ethanol was added along with a few drops (5-6) of 1M tetramethyl ammonium hydroxide (TMAH) solution in ethanol. The mixture was then heated at 40-45° C. for several hours under nitrogen atmosphere with stirring, followed by precipitation of QDs using chloroform and hexane mixture. Following removal of the solvents, the QDs were dispersed in DI water and excess solubilized free ligands were removed by applying a few rounds of concentration dilution using a membrane filtration device Amicon Ultra 50K (from Millipore).

Figure 4A:
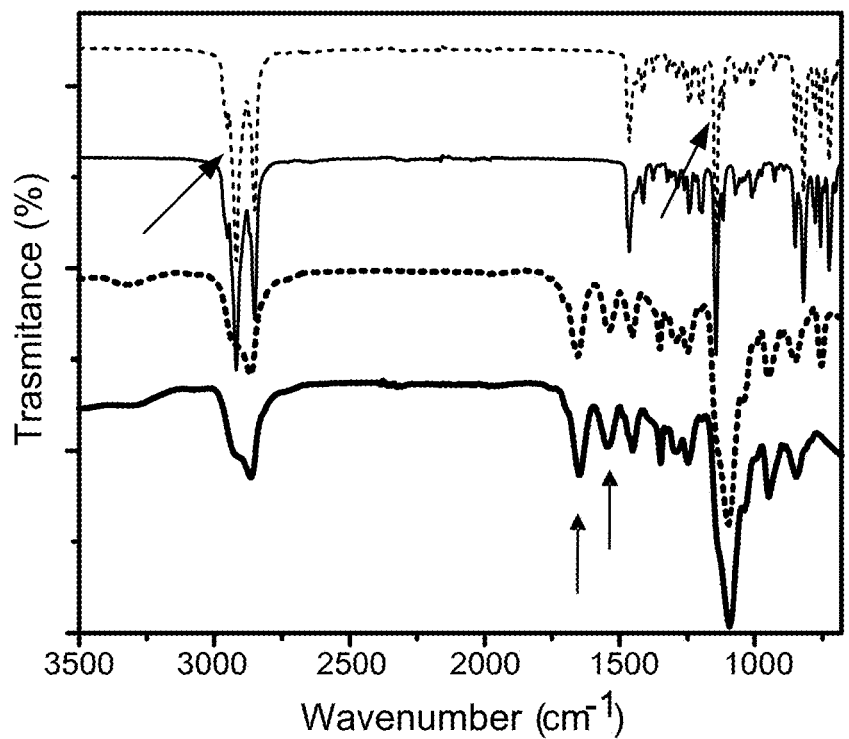
Figure 4B:
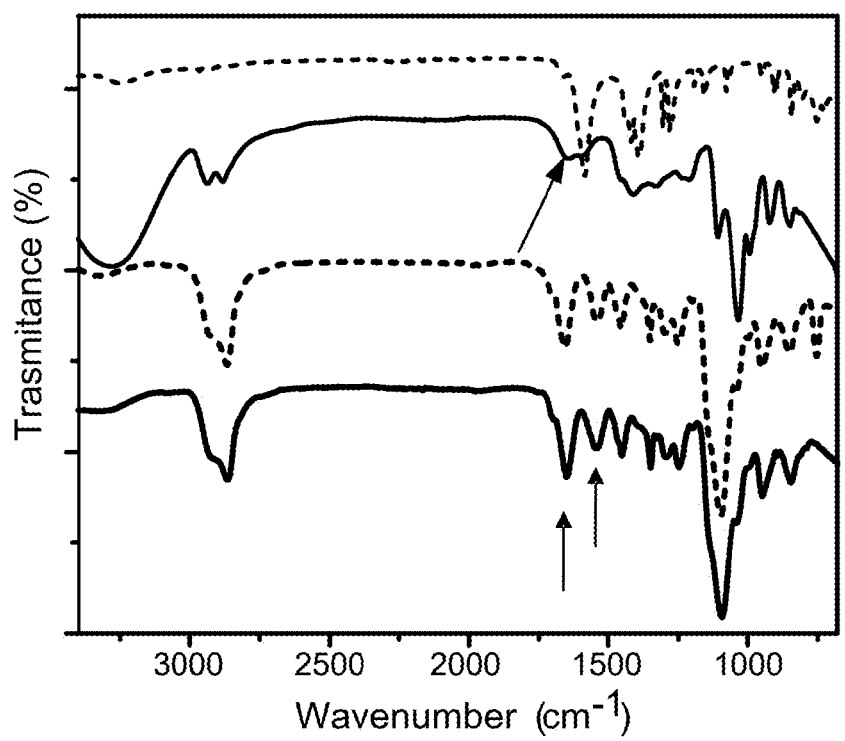

The ligand exchange on the QD was confirmed using FT-IR spectra (see FIG. 4). The spectra show that the bands characteristic of TOP/TOPO have disappeared following cap exchange, while new bands at ~1648 cm$^{-1}$ (ascribed to amide I, C=O stretching) and at ~1546.7 cm$^{-1}$ (ascribed to amide II, N—H bending) were measured. Moreover, the spectrum of the OligoPEG-capped QDs is identical to that collected from the pure ligand.

Figure 5:
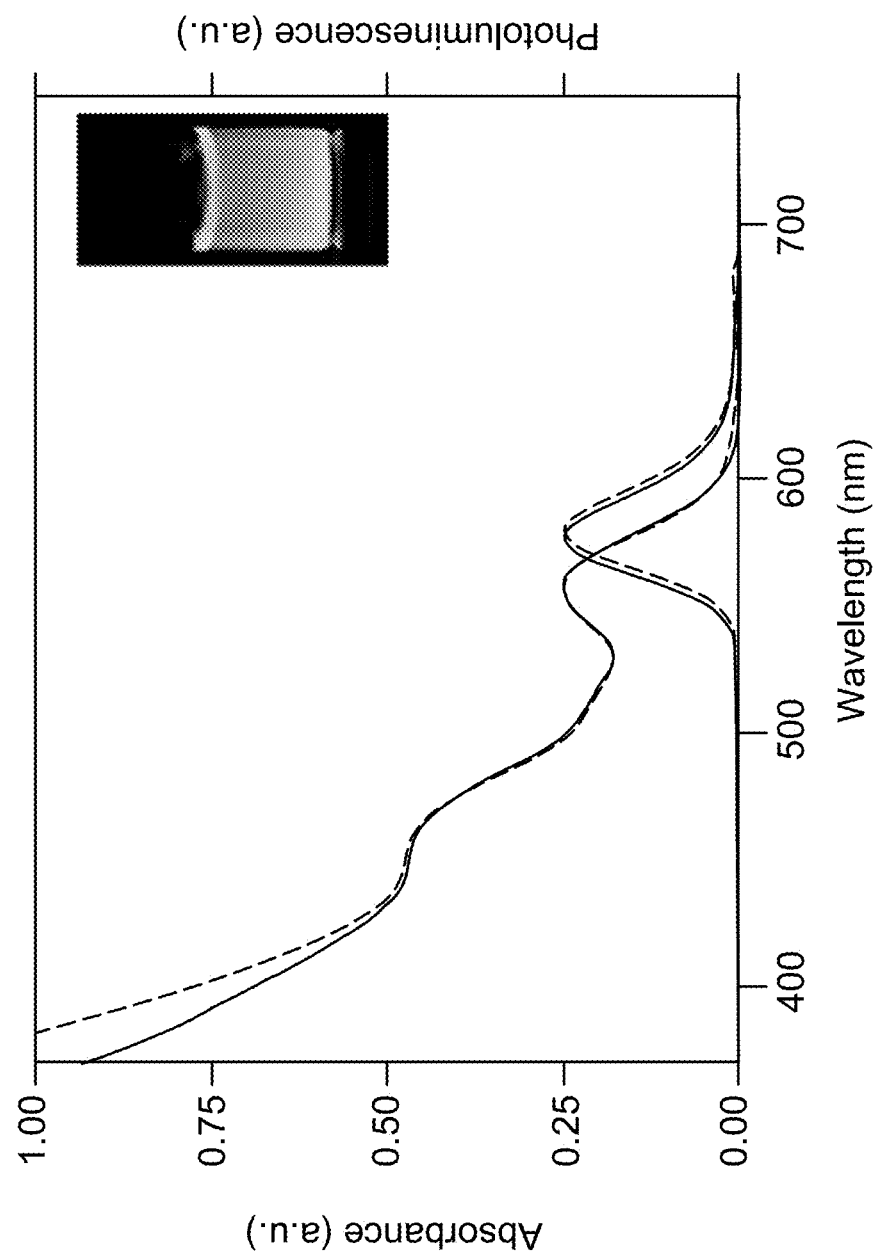
FIG. 5 shows absorption and fluorescence spectra of QDs ($\lambda_{ex}$=575 nm) in toluene (solid line) and in water (broken line) after ligand exchange with OligoPEG ligand 5B; $\lambda_{ex}$=350 nm; the inset shows the fluorescence image of a yellow emitting QD dispersion capped with OligoPEG-DHLA (Compound 5B) in phosphate-buffered saline (PBS) at neutral pH. The UV-Vis and PL spectra were normalized with respect to the band edge peak and maximum emission, respectively.

The absorption and emission spectra of the QDs (FIG. 5) were essentially unaffected by the transfer to buffer media as shown for dispersions of TOP/TOPO-capped (in toluene) and OligoPEG-capped QDs (in DI water). This implies that cap exchange with the new OligoPEG does not alter any of the optical and spectroscopic properties of the nanocrystals, as was reported with DHLA-PEG ligands. Transfer to aqueous media was nonetheless accompanied by a loss in PL yield (~25-50% decrease in PL signal) compared to the native TOP/TOPO-capped QDs in toluene. This reduction has been commonly reported for QDs cap-exchanged with thiol-appended ligands including DHLA-PEG series.[40,41,58,61,62]

Cap exchange of citrate-stabilized AuNPs could be realized using both sets of oligomers, TA- and DHLA-appended, similar to what was reported with the molecular scale PEGylated ligands.[63] In a typical cap exchange, the required amount of OligoPEG-TA (4B, 110 mg) was diluted in 1 mL of DI water and the solution was adjusted to pH=10 by adding a drop of 0.5 M NaOH. This solution was added to citrate-stabilized AuNPs (4 mL, ~1.4×10$^{12}$ particles/mL) and the dispersion stirred overnight (~18 h) at room temperature.[63] The mixture was then filtered through a 0.45 µm hydrophilic membrane, and excess ligand was removed by washing 2-3 times with DI water using a centrifugal filtration device (Millipore, $M_W$ cut-off of 50 kDa), as described above.

Cap-exchange of the AuNPs with OligoPEGs (e.g., 4B, and 5B) was characterized by FT-IR and absorption spectroscopy. FT-IR data collected from AuNP dispersions after cap exchange showed the presence of the amide I band (~1652 cm$^{-1}$) and amide II band (~1540.2 cm$^{-1}$); similar to QDs the characteristic features of the ligands remained intact after coordinating with the Au surfaces. We also measured no change in the UV/Vis-absorption spectra of AuNPs after ligand exchange. We should note that there is a small contribution to the UV-Vis absorption spectrum (for $\lambda$<400 nm) of the hydrophilic OligoPEG-QDs due to the PAA.

4. Colloidal Stability of OligoPEG-Capped QDs and AuNPs

We tested the stability of aqueous dispersions of OligoPEG-capped nanoparticles over a broad pH range and in the presence of a large excess of NaCl. Previous reports show that ligand exchange of QDs with DHLA-PEG moieties provided long-term colloidal stability in buffer solutions over the pH range from 4-11.[40,57] A slightly broader pH window (3-12) was achieved using those PEGylated ligands with gold nanoparticles.[57] Therefore, in this study we focused on the stability of nanoparticles in phosphate buffer media under extreme conditions (pH=2 and pH=14) and in the presence of a large excess of electrolytes (2 M NaCl). Phosphate buffers at pH range 2-12 were prepared following standard procedures using different molar ratio of NaH$_2$PO$_4$, Na$_2$HPO$_4$, Na$_3$PO$_4$ or H$_3$PO$_4$, and then a few drops of either HCl or NaOH were added to adjust the extreme pHs such as (pH=2, pH=13 and pH=14). Each buffer solution contained 0.137 mM NaCl. Aliquots of stock solutions of OligoPEG-capped NPs (~6 µM) were added to the desired buffer to a final concentration of 1 µM and 3 nM for QDs and AuNPs, respectively. Dispersions of DHLA-PEG-OCH$_3$- or TA-PEG-OCH$_3$-stabilized nanocrystals at several pHs (at similar concentrations) were used as control. Green, yellow and red emitting OligoPEG-stabilized QDs and AuNPs were used for the pH stability test.

Figures 6A, 6B:
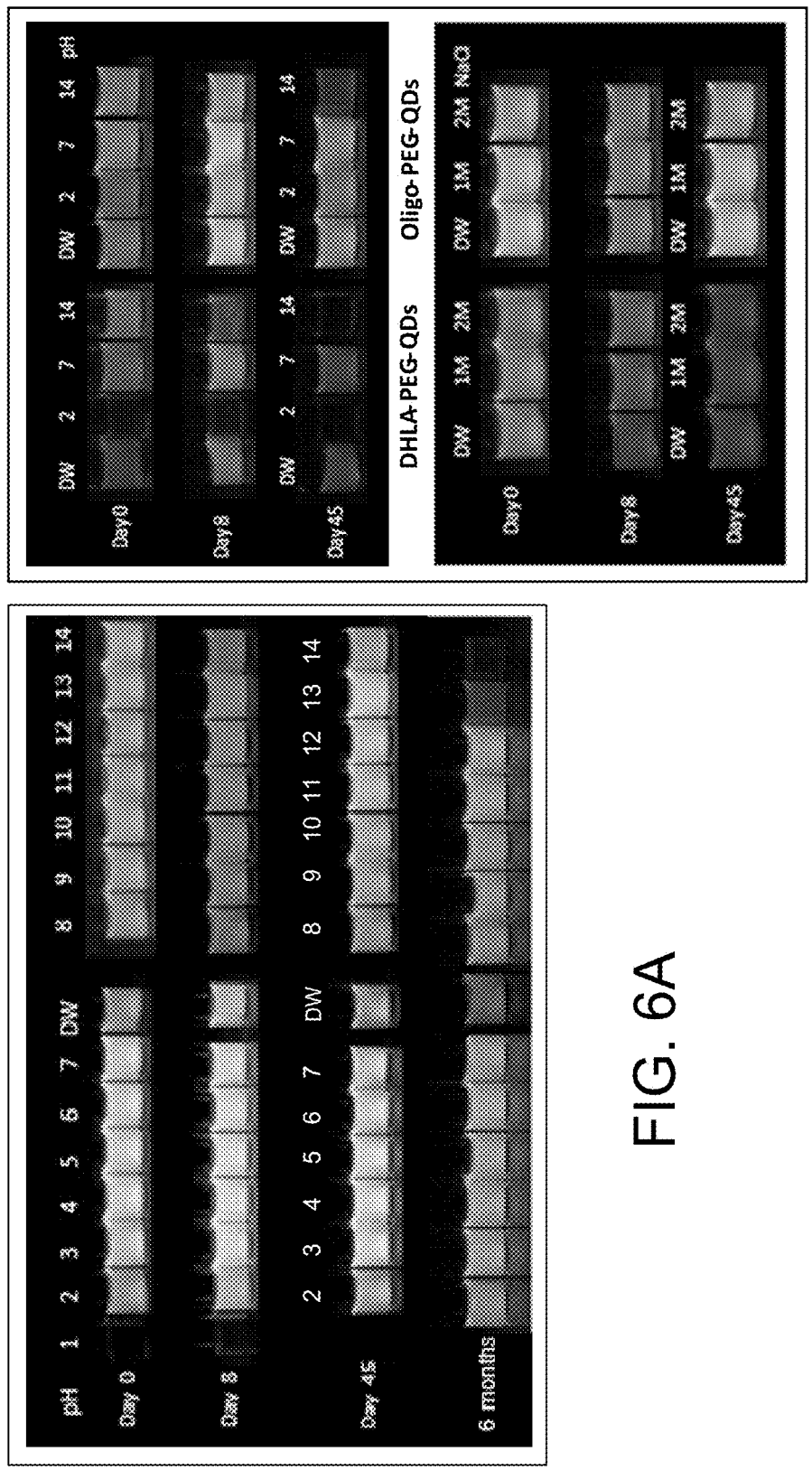
FIG. 6A shows fluorescence images of CdSe—ZnS QDs ($\lambda_{em}$=575 nm) capped with OligoPEG-DHLA ligand (5B) at different pH values and control sample in deionized water (DW); each vial contains 1 μM QDs in phosphate buffer. No sign of aggregation is observed after 45 days of storage.
FIG. 6B shows the fluorescence images of QDs stabilized by both DHLA-PEG-OCH$_3$ and OligoPEG-DHLA at three different pHs (2, 7 and 14) (top) and fluorescence images of QDs stabilized by both DHLA-PEG-OCH$_3$ and OligoPEG-DHLA in the presence of 1M and 2M NaCl (bottom).

FIG. 6a shows the fluorescence images of a set of yellow emitting QDs capped with OligoPEG-DHLA (5B) at pH values ranging from 2 to 14 in phosphate buffer solutions, immediately following transfer and after 45 days of storage. FIG. 6b shows a side-by-side comparison of the same water-dispersed QDs capped with either 5B or DHLA-PEG-OCH$_3$ ligands at three different pH (2, 7, and 14), and in the presence of 1 and 2 M NaCl. The images indicate that the QD dispersions remained homogeneous and optically clear over the full range of pHs and in the presence of 2M NaCl. We should emphasize that the long term colloidal stability of the QD dispersions is also accompanied with little to no change in the fluorescence emission. Overall relative variation in the fluorescence intensity was small (smaller than 20% after 1 year in the worse case), and it varied from one pH to another. Nonetheless, though the samples at pH=2-13 remained homogeneous and fluorescent for at least 6 months of storage. The dispersion at pH=14 became slightly reddish, and turbidity slowly formed after 3 months, indicative of slow aggregation built up. In comparison, nanoparticles capped with DHLA-PEG became unstable at pH=2 and 14 after 8 days of storage (FIG. 6b). The control dispersions of DHLA-PEG-QDs stayed stable in the presence of excess NaCl, though a slight color change could be seen. Similar long term stability was observed for QDs dispersed in the growth media (see Supporting Information).

We also verified that other color QDs cap-exchanged with the OligoPEG ligand 5B (green emitting with $\lambda_{em}$=543 nm and red emitting with $\lambda_{em}$=617 nm) were also stable and fluorescent over the pH range 2-13 for at least 3 months. These observations combined clearly indicate that the nanoparticle coatings of the invention tightly bind onto the QDs surface and promote their long term stability in a wide range of buffers and in the presence of large excess of electrolytes.

Similar to QDs, AuNPs capped with these nanoparticle coatings exhibited remarkable stability to pH changes and to added NaCl, with no sign of aggregation or changes in the optical absorption spectra for at least 8 months (see FIG. 7). We also tested the stability of the AuNPs in the presence of DTT molecules; AuNPs capped with compound 4A and compound 4B along with NPs capped with TA-PEG-OCH$_3$ (control) were used. Enhanced NP stability is achieved using compounds 4A and 4B compared to control samples. Nonetheless, stability is slightly better for NP capped with 4A. We suspect that this may be due to the larger number of TA groups in compound 4B compared to 4A, which can cause sulfur-sulfur cross bridging and potential aggregation in the presence of DTT.

5. Surface Functionalization of Quantum Dots

Figure 8A:
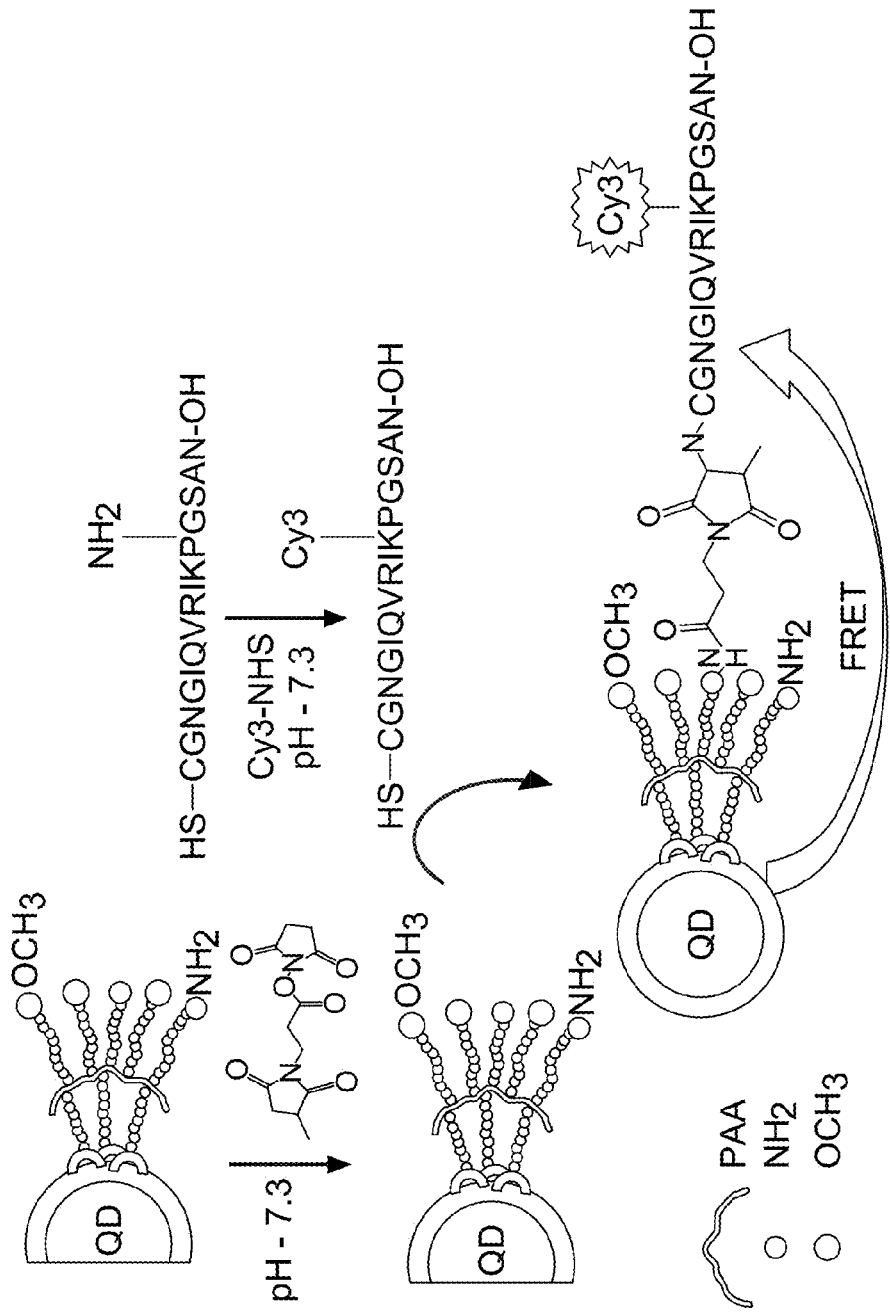
FIG. 8A shows Schematic representation (not to scale) of the coupling strategy used to attach the OligoPEG-DHLA-capped QDs ($\lambda_{em}$=543 nm) with peptide molecules pre-labelled with Cy3 dye.

The synthetic strategy also allows easy introduction of functional groups within the ligand structure and the preparation of nanoparticles that present varying numbers of reactive groups on their surfaces. This offers an alternative scheme to those previously described using molecular scale DHLA-PEG-based ligands, where end-functionalized and inert ligands were mixed (during cap exchange) in order to achieve surface reactivity.[42] In a preliminary demonstration we used and OligoPEG-DHLA ligand presenting a fraction of grafted NH$_2$-PEG moieties (compound 7A and 7B), and tested whether those amine groups were available for further reactions. FIG. 8 shows a gel electrophoresis image for four dispersions of green emitting QDs, three cap exchanged with OligoPEG 5B, 7A, and 7B, while the fourth was capped with DHLA-PEG-OCH$_3$ (as control).

The QD dispersions were diluted in a 20% glycerol 1×TBE loading buffer (pH 8.5), loaded into 1% agarose gel, then 7.5 V/cm was applied for 30 min. The gel was imaged using Bio-Rad Chemidoc Gel Imaging System. The image in FIG. 8 shows a marginal mobility shift toward the anode for QDs capped with OligoPEG 5B while no shift was measured for DHLA-PEG-OCH$_3$-capped QDs (lane 1 and 2), indicating that the nanoparticles cap exchanged with 5B presented a very small negative surface density (i.e., essentially neutral nanoparticles). This is somewhat surprising given the fact that the $^1$H NMR data indicated that there are one or two uncoupled carboxyl groups along the PAA in the final OligoPEG 5A and 5B, and may imply that these groups are completely "shielded" inside the oligomer structure.

Figure 8B:
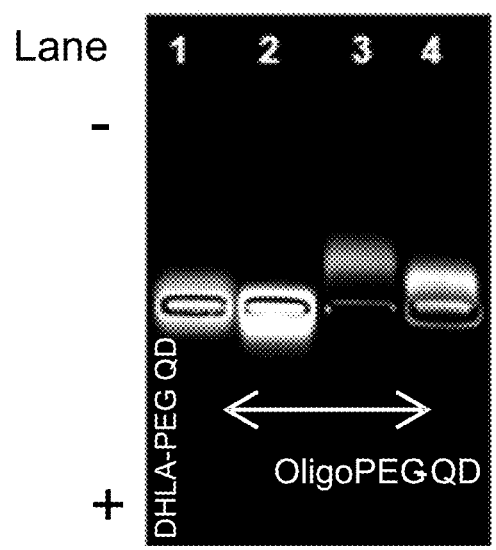
FIG. 8B shows gel eletrophoresis image of QDs capped with OligoPEG ligands. In lane 1 the QDs are capped with DHLA-PEG-OCH$_3$ (control). In lane 2 the QDs are capped with 5B. In lane 3, the QDs are capped with 7B (OligoPEG containing ~10% amines). In lane 4, the QDs are capped with 7A (OligoPEG containing ~6% amines).

In contrast, QDs capped with OligoPEG ligands (7A and 7B) designed with a small fraction of aminated PEG moieties (5% and 10% of the total number of PAA monomers) exhibited a mobility shift towards the negative electrode, with slightly larger shift measured for ligands presenting 10% aminated PEG moieties (see lanes 3 and 4 in FIG. 8b). This proves that tunable numbers of amines on the nanocrystal are available for further coupling to potential target molecules.

6. QD-Peptide-Dye Conjugates and Energy Transfer Measurements

We further used a combination of absorption spectroscopy and FRET (fluorescence resonance energy transfer) measurements to extract an estimate for the number of amine groups available on a QD cap exchanged with compound 7A (amine-OligoPEG-DHLA). For this 543 nm emitting QDs cap exchanged with compound 7A were conjugated to Cy3-labeled peptides as follows (see schematics in FIG. 8): 1) Amines on the QDs were transformed to maleimide groups using NHS-methyl maleimide, to make the nanocrystal surface compatible with cysteine coupling chemistry; 2) NHS-Cy3 was conjugated to the lysine (K) group on a peptide presenting a N-terminal cysteine (SEQ ID NO 1: CGNGIQVRIKPGSAN); 3) following purification the Cy3-peptide was reacted with maleimide-QDs to yield QD-peptide-Cy3 complexes.

Figure 8C:
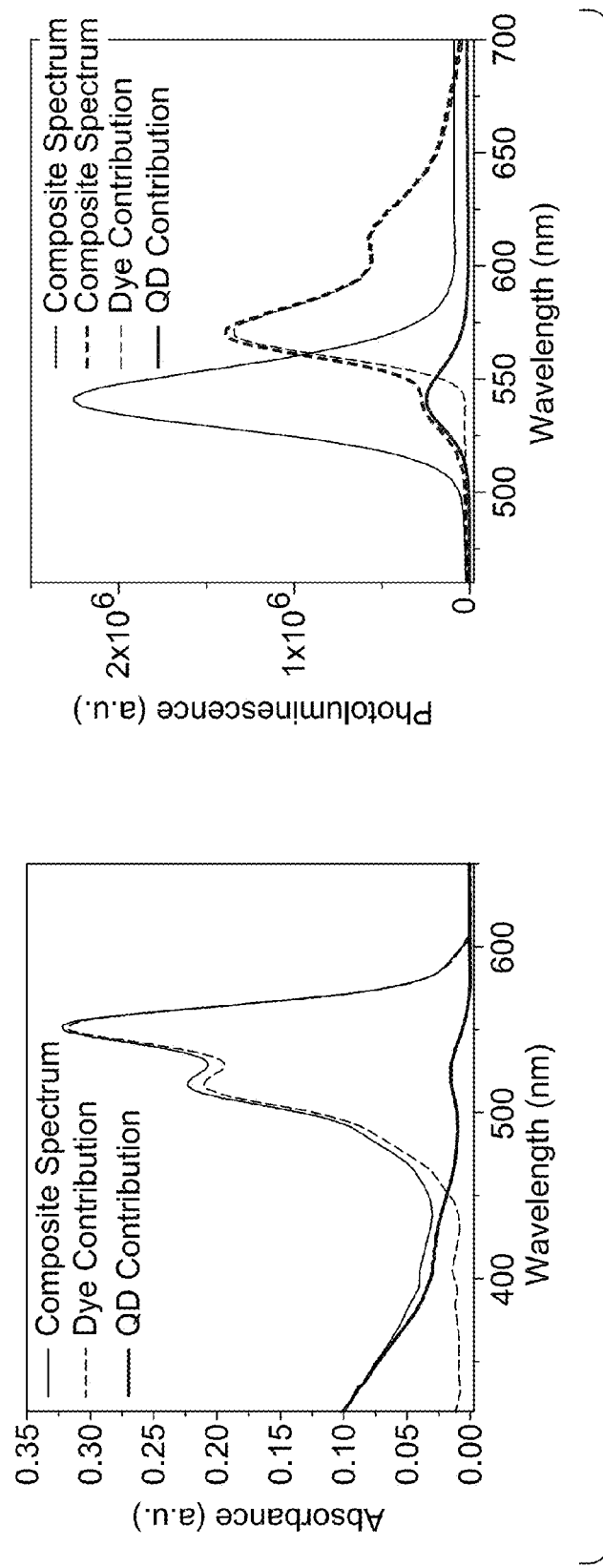
FIG. 8C shows UV-Vis absorption spectra of QD-Peptide-Cy3 conjugate after purification together with the deconvoluted contributions of pure QDs and Cy3 dye (left) and composite emission spectra of QD-Peptide-Cy3 conjugate, together with the deconvoluted contributions from QDs and Cy3 dye (right). The dispersion was excited at 430 nm, where direct dye excitation is very small.

FIG. 8c shows the UV-Vis absorption (left) and the photoluminescence (right) spectra collected for a dispersion of QD-peptide-dye conjugates. Both composite spectra show clear contribution from the QD and dye. The absorption spectrum could be deconvoluted to yield the individual contributions of the QDs and Cy3 dye in the sample. From the absorption data and using the available extinction coefficients of both dye (150,000 M$^{-1}$ cm$^{-1}$ at $\lambda$=550 nm) and QDs (7.06×10$^5$ at $\lambda$=350 nm) we extracted a measure for the molar concentrations of QDs and dye in the dispersion, which we used to deduce an estimate for the average number of Cy3 dyes per QD n ~22.

Absorption data alone do not necessary prove coupling of the dye to QDs, however. Analysis of the FRET data, though more complex, is more informative because only close proximity between QD and dye (due to conjugation) can produce sizable rates of FRET.[64] FIG. 8c shows that following coupling between amine-QD and Cy3-peptide, there is a substantial loss in the QD contribution (compared to QD only control dispersion) coupled with a pronounced enhancement in the dye contribution; direct excitation contribution to the dye emission, subtracted from the composite spectrum, is small as we excite the system far from the dye peak.[65]

These observations were further supported by time-resolved fluorescence measurements, where a substantial decrease in the exciton lifetime of the QDs (donor) was measured for the conjugates. A quantitative estimate of the lifetime changes is difficult, nonetheless, due to the sizable spectral overlap between QD and dye emissions. We attribute these results (PL data shown in FIG. 8c and time resolved data to non radiant transfer of excitation energy from the QD (donor) to proximal dyes, as a result of conjugate formation.

The FRET efficiency E is measured experimentally using:

$$E = \frac{F_D - F_{DA}}{F_D} \qquad \text{EQ. (1)}$$

where $F_D$ and $F_{DA}$ are the fluorescence intensities collected from the donor alone and donor in the presence of the acceptor(s), respectively. To extract an estimate for the value of n, we use a simplified expression of the FRET efficiency we previously demonstrated for a centro-symmetric system (made of one central donor and n acceptors, all arrayed at a given separation distance, r, from the center of the donor), $E_n$, expressed as:[65]

$$E = \frac{nR_0^6}{nR_0^6 + r^6}$$  EQ. (2)

where the Förster radius, $R_0$, designates the separation distance (for one-donor-one-acceptor system) corresponding to $E_{n=1}=0.5$, and is given by:[64]

$$R_0^6 = (9.78 \times 10^3 n_D^{-4} \kappa_p^2 Q_D I)$$  EQ. (3)

$R_0$ (expressed in Å) depends on the PL quantum yield of the donor, $Q_D$, the refractive index of the medium $n_D$, the Avogadro's number, $N_A$, and the dipole orientation parameter, $\kappa_p$, and the spectral overlap integral, I.[64] The orientation factor $\kappa_p^2 = 2/3$ for our present configuration. I is extracted from integration (over all wavelengths) of the spectral overlap function, $J(\lambda) = PL_{D\text{-}corr}(\lambda) \times \lambda^4 \times \epsilon_A$; where $PL_D$ and $\epsilon_A$ designate the normalized fluorescence spectrum of the donor and the extinction coefficient spectrum of the acceptor, respectively.[64] Though most of the parameters in the expression for $E_n$ are extracted from the experimental data, a judicious consideration of the conjugate configuration and estimation of r are important, as they play an important role in extracting a value for n, due to the sixth power dependence of $E_n$ on r. Table 3 shows the values for the various experimental parameters used for the present analysis.

For our system, we use an estimate for the separation distance r ~67 Å (assuming a QD radius of ~30 Å, a capping layer of ~20 Å, a peptide sequence of ~12 Å; we assume that the dye center is located at 5 Å from the linker site). Using this information we estimate that there are ~21 Cy3 dyes per QD-assembly.[65,66] This value is very close to the one estimated form the UV-Vis data above. If we assume a complete maleimide transformation of all the amines on the QD and 100% coupling efficiency between the cysteines and maleimides, we anticipate that green emitting core-shell QDs cap exchanged with OligoPEG-DHLA (7A) presents ~20 amine reactive sites. This is certainly an underestimated value, as the reactions involved are naturally less than 100% efficient. Nonetheless, the consistency of the estimates extracted from the spectroscopy data implies that the reactive amines in the oligomer structure are available for further modification and coupling to target biomolecules.

7. Experimental Details

Materials.

All syntheses described in this study were carried out under $N_2$ passed through an $O_2$ scrubbing tower unless otherwise stated. Standard Schlenk techniques were used when manipulating air-sensitive reactions, while air sensitive materials were handled in an MBraun Labmaster 130 glovebox (Stratham, N.H.). Polyacrylic acid (PAA, Molecular weight average ~1800), poly(ethylene glycol) (Molecular weight average of 600 and 750), triphenylphosphine, thioctic acid, DMAP (4-(N,N-dimethylamino) pyridine), DCC (N,N-dicylohexylcarbodiimide), triethylamine, sodium borohydride, methanesulfonyl chloride, organic solvents (DMF, $CHCl_3$, etc), PBS buffer and salts (such as NaCl, $Na_2SO_4$, $Mg_2SO_4$) were purchased from Sigma Chemicals (St. Louis, Mo.). Sodium azide was purchased from Alfa Aesar (Ward Hill, Mass.). The chemicals and solvents were used as purchased unless otherwise specified. Deuterated solvents were purchased from Cambridge Isotope Laboratories (Andover, Mass.) and used as received. Column purification chromatography was performed using silica gel (60 Å, 230-400 mesh, from Bodman Industries, Aston, Pa.). The mono reactive N-hydroxysulfosuccinimide (sulfo-NHS)-Cy3 dye and the PD10 column were purchased from GE Healthcare (Piscataway, N.J.), while the peptide was acquired from Peptide International (Louisville, Ky.). The molar amounts of the PEG derivatives were calculated using the average molecular weight of the corresponding PEG (e.g., PEG ~600 or 750).

Instrumentation.

$^1$H NMR spectra of all compounds were recorded using 600 MHz spectrometer (Bruker SpectroSpin 600 MHz). FT-IR spectra of the final purified compounds were measured from PerkinElmer FT-IR spectrometer. Optical absorption measurements were carried out using a Shimadzu UV-Vis absorption spectrophotometer (UV 2450 model), while the fluorescence spectra were collected on Fluorolog-3 spectrometer (Jobin Yvon Inc., Edison, N.J.) equipped with PMT and CCD detectors. Solvent evaporation was carried using a lab-scale Buchi rotary evaporator R-215 (New Castle, Del.).

The invention has been described above with reference to the accompanying drawings, in which preferred embodiments of the invention are shown. Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described. The skilled should understand that the methods and materials used and described are examples and may not be the only ones suitable for use in the invention.

In the specification set forth above there have been disclosed typical preferred embodiments of the invention, and although specific terms are employed, the terms are used in a descriptive sense only and not for purposes of limitation. The invention has been described in some detail, but it will be apparent that various modifications and changes can be made within the spirit and scope of the invention as described in the foregoing specification and as defined in the appended claims.

REFERENCES

The following references are all incorporated herein by reference in their entirety. Furthermore, where a definition or use of a term in a reference, which is incorporated by reference herein is inconsistent or contrary to the definition of that term provided herein, the definition of that term provided herein applies and the definition of that term in the reference does not apply.

(1) Alivisatos, A. P. *Science* 1996, 271, 933.
(2) Murray, C. B.; Kagan, C. R.; Bawendi, M. G. *Annu. Rev. Mater. Sci.* 2000, 30, 545.
(3) Klimov, V. I.; Mikhailovsky, A. A.; Xu, S.; Malko, A.; Hollingsworth, J. A.; Leatherdale, C. A.; Eisler, H. J.; Bawendi, M. G. *Science* 2000, 290, 314.
(4) Malko, A. V.; Mikhailovsky, A. A.; Petruska, M. A.; Hollingsworth, J. A.; Htoon, H.; Bawendi, M. G.; Klimov, V. I. *Appl. Phys. Lett.* 2002, 81, 1303
(5) Nozik, A. J.; Beard, M. C.; Luther, J. M.; Law, M.; Ellingson, R. J.; Johnson, J. C. *Chem. Rev.* 2010, 110, 6873.
(6) Li, L.; Yang, X. C.; Gao, J. J.; Tian, H. N.; Zhao, J. Z.; Hagfeldt, A.; Sun, L. C. *J. Am. Chem. Soc.* 2011, 133, 8458.

(7) Chen, C. Y.; Cheng, C. T.; Lai, C. W.; Wu, P. W.; Wu, K. C.; Chou, P. T.; Chou, Y. H.; Chiu, H. T. *Chem. Commun.* 2006, 263.

(8) Raymo, F. M.; Yildiz, I. *Phys. Chem. Chem. Phys.* 2007, 9, 2036.

(9) Medintz, I. L.; Uyeda, H. T.; Goldman, E. R.; Mattoussi, H. *Nat. Mater.* 2005, 4, 435.

(10) Michalet, X.; Pinaud, F. F.; Bentolila, L. A.; Tsay, J. M.; Doose, S.; Li, J. J.; Sundaresan, G.; Wu, A. M.; Gambhir, S. S.; Weiss, S. *Science* 2005, 307, 538.

(11) Biju, V.; Itoh, T.; Ishikawa, M. *Chem. Soc. Rev.* 2010, 39, 3031.

(12) Zrazhevskiy, P.; Sena, M.; Gao, X. H. *Chem. Soc. Rev.* 2010, 39, 4326.

(13) Pinaud, F.; Clarke, S.; Sittner, A.; Dahan, M. *Nat Meth* 2010, 7, 275.

(14) Mattoussi, H.; Cheon, J. Editors, *Inorganic Nanoprobes for Biological Sensing and Imaging*; Artech House, 685 Canton St, Norwood, Ma 02062 USA, 2009.

(15) Jaiswal, J. K.; Mattoussi, H.; Mauro, J. M.; Simon, S. M. *Nat. Biotechnol.* 2003, 21, 47.

(16) Gao, X. H.; Cui, Y. Y.; Levenson, R. M.; Chung, L. W. K.; Nie, S. M. *Nat. Biotechnol.* 2004, 22, 969.

(17) Henglein, A. *Berichte der Bunsengesellschaft für physikalische Chemie* 1982, 86, 301.

(18) Rossetti, R.; Ellison, J. L.; Gibson, J. M.; Brus, L. E. *J. Chem. Phys.* 1984, 80, 4464.

(19) Murray, C. B.; Norris, D. J.; Bawendi, M. G. *J. Am. Chem. Soc.* 1993, 115, 8706.

(20) a) Hines, M. A. and Guyot-Sionnest, P. *J. Phys. Chem.* 1996, 100, 468. b) Dabbousi, B. O.; Rodriguez-Viejo, J.; Mikulec, F. V.; Heine, J. R.; Mattoussi, H.; Ober, R.; Jensen, K. F.; Bawendi, M. G. *J. Phys. Chem. B* 1997, 101, 9463.

(21) Peng, Z. A.; Peng, X. G. *J. Am. Chem. Soc.* 2001, 123, 183.

(22) Rogach, A.; Kershaw, S. V.; Burt, M.; Harrison, M. T.; Kornowski, A.; Eychmuller, A.; Weller, H. *Adv. Mater.* 1999, 11, 552.

(23) Rogach, A. L.; Kornowski, A.; Gao, M.; Eychmüller, A.; Weller, H. *J. Phys. Chem. B* 1999, 103, 3065.

(24) Allen, P. M.; Bawendi, M. G. *J. Am. Chem. Soc.* 2008, 130, 9240.

(25) Pons, T.; Pic, E.; Lequeux, N.; Cassette, E.; Bezdetnaya, L.; Guillemin, F.; Marchal, F.; Dubertret, B. *ACS Nano* 2010, 4, 2531.

(26) van Embden, J.; Jasieniak, J.; Mulvaney, P. *J. Am. Chem. Soc.* 2009, 131, 14299.

(27) Turkevich, J.; Stevenson, P. C.; Hillier, J. *Discuss. Faraday Soc.* 1951, 11, 55.

(28) Frens, G. *Nature-Physical Science* 1973, 241, 20.

(29) Bruchez, M.; Moronne, M.; Gin, P.; Weiss, S.; Alivisatos, A. P. *Science* 1998, 281, 2013.

(30) Gerion, D.; Pinaud, F.; Williams, S. C.; Parak, W. J.; Zanchet, D.; Weiss, S.; Alivisatos, A. P. *J. Phys. Chem. B* 2001, 105, 8861.

(31) Hu, S.-H.; Gao, X. H. *Adv. Func. Mater.* 2010, 20, 3721.

(32) Dubertret, B.; Skourides, P.; Norris, D. J.; Noireaux, V.; Brivanlou, A. H.; Libchaber, A. *Science* 2002, 298, 1759.

(33) Pellegrino, T.; Manna, L.; Kudera, S.; Liedl, T.; Koktysh, D.; Rogach, A. L.; Keller, S.; Rädler, J.; Natile, G.; Parak, W. J. *Nano Lett.* 2004, 4, 703.

(34) Carion, O.; Mahler, B.; Pons, T.; Dubertret, B. *Nat. Protoc.* 2007, 2, 2383.

(35) Yu, W. W.; Chang, E.; Falkner, J. C.; Zhang, J.; Al-Somali, A. M.; Sayes, C. M.; Johns, J.; Drezek, R.; Colvin, V. L. *J. Am. Chem. Soc.* 2007, 129, 2871.

(36) Lees, E. E.; Nguyen, T.-L.; Clayton, A. H. A.; Mulvaney, P. *ACS Nano* 2009, 3, 1121.

(37) Kim, S.-W.; Kim, S.; Tracy, J. B.; Jasanoff, A.; Bawendi, M. G. *J. Am. Chem. Soc.* 2005, 127, 4556.

(38) Wu, X.; Liu, H.; Liu, J.; Haley, K. N.; Treadway, J. A.; Larson, J. P.; Ge, N.; Peale, F.; Bruchez, M. P. *Nat Biotech* 2003, 21, 41.

(39) Mattoussi, H.; Mauro, J. M.; Goldman, E. R.; Anderson, G. P.; Sundar, V. C.; Mikulec, F. V.; Bawendi, M. G. *J. Am. Chem. Soc.* 2000, 122, 12142.

(40) Susumu, K.; Uyeda, H. T.; Medintz, I. L.; Pons, T.; Delehanty, J. B.; Mattoussi, H. *J. Am. Chem. Soc.* 2007, 129, 13987.

(41) Liu, W.; Howarth, M.; Greytak, A. B.; Zheng, Y.; Nocera, D. G.; Ting, A. Y.; Bawendi, M. G. *J. Am. Chem. Soc.* 2008, 130, 1274.

(42) Susumu, K.; Mei, B. C.; Mattoussi, H. *Nat. Protoc.* 2009, 4, 424.

(43) Jung, J.; Solanki, A.; Memoli, K. A.; Kamei, K-I.; Kim, H.; Drahl, M. A.; Williams, L. J.; Tseng, H-R.; Lee, K-B. *Angew. Chem. Int. Ed.* 2010, 49 103.

(44) Liu, W.; Greytak, A. B.; Lee, J.; Wong, C. R.; Park, J.; Marshall, L. F.; Jiang, W.; Curtin, P. N.; Ting, A. Y.; Nocera, D. G.; Fukumura, D.; Jain, R. K.; Bawendi, M. G. *J. Am. Chem. Soc.* 2010, 132, 472.

(45) Lee, J. H.; Huh, Y. M.; Jun, Y.; Seo, J.; Jang, J.; Song, H. T.; Kim, S.; Cho, E. J.; Yoon, H. G.; Suh, J. S.; Cheon, J. *Nat Med* 2007, 13, 95.

(46) Thomas, C. R.; Ferris, D. P.; Lee, J. H.; Choi, E.; Cho, M. H.; Kim, E. S.; Stoddart, J. F.; Shin, J. S.; Cheon, J.; Zink, J. I. *J. Am. Chem. Soc.* 2010, 132, 10623.

(47) Stewart, M. H.; Susumu, K.; Mei, B. C.; Medintz, I. L.; Delehanty, J. B.; Blanco-Canosa, V J. B.; Dawson, P. E.; Mattoussi, H. *J. Am. Chem. Soc.* 2010, 132, 9804.

(48) Muro, E.; Pons, T.; Lequeux, N.; Fragola, A.; Sanson, N.; Lenkei, Z.; Dubertret, B. *J. Am. Chem. Soc.* 2010, 132, 4556.

(49) Lees, E. E.; Gunzburg, M. J.; Nguyen, T.-L.; Howlett, G. J.; Rothacker, J.; Nice, E. C.; Clayton, A. H. A.; Mulvaney, P. *Nano Lett.* 2008, 8, 2883.

(50) Bhang, S. H.; Won, N.; Lee, T.-J.; Jin, H.; Nam, J.; Park, J.; Chung, H.; Park, H.-S.; Sung, Y.-E.; Hahn, S. K.; Kim, B.-S.; Kim, S. *ACS Nano* 2009, 3, 1389.

(51) Liu, L.; Guo, X.; Li, Y.; Zhong, X. *Inorg. Chem.* 2010, 49, 3768.

(52) Yildiz, I.; McCaughan, B.; Cruickshank, S. F.; Callan, J. F.; Raymo, F. M. *Langmuir* 2009, 25, 7090.

(53) Yildiz, I.; Deniz, E.; McCaughan, B.; Cruickshank, S. F.; Callan, J. F.; Raymo, F. M. *Langmuir* 2010, 26, 11503.

(54) Shen, H. Y.; Jawaid, A. M.; Snee, P. T. *ACS Nano* 2009, 3, 915.

(55) Clapp, A. R.; Goldman, E. R.; Mattoussi, H. *Nat. Protocols* 2006, 1, 1258.

(56) Qu, L. H; Peng, Z. A.; Peng, X. G. *Nano Letters* 2001, 1, 333.

(57) Mei, B. C.; Susumu, K.; Medintz, I. L.; Delehanty, J. B.; Mountziaris, T. J.; Mattoussi, H. *J. Mater. Chem.* 2008, 18, 4949.

(58) Uyeda, H. T.; Medintz, I. L.; Jaiswal, J. K.; Simon, S. M.; Mattoussi, H. *J. Am. Chem. Soc.* 2005, 127, 3870.

(59) Anderson, R. E.; Chan, W. C. W. *ACS Nano* 2008, 2, 1341.

(60) Choi, C. H. J.; Alabi, C. A.; Webster, P.; Davis, M. E. *Proc. Natl. Acad. Sci. U.S.A.* 2010, 107, 1235.

(61) Bullen, C.; Mulvaney, P. *Langmuir* 2006, 22, 3007.

(62) Munro, A. M.; Jen-La Plante, I.; Ng, M. S.; Ginger, D. S. *J. Phys. Chem. C* 2007, 111, 6220.
(63) Mei, B. C.; Oh, E.; Susumu, K.; Farrell, D.; Mountziaris, T. J.; Mattoussi, H. *Langmuir* 2009, 25, 10604.
(64) Lakowicz, J. R. *Principles of fluorescence spectroscopy;* 2nd ed.; Kluwer Academic/Plenum: New York, 1999.
(65) Clapp, A. R.; Medintz, I. L.; Mauro, J. M.; Fisher, B. R.; Bawendi, M. G.; Mattoussi, H. *J. Am. Chem. Soc.* 2004, 126, 301.
(66) Medintz, I. L.; Clapp, A. R.; Brunel, F. M.; Tiefenbrunn, T.; Uyeda, H. T; Chang, E. L.; Deschamps, J. R.; Dawson, P. E.; Mattoussi, H. *Nat Mater* 2006, 5, 581.
(67) Na, H. B.; Palui, G.; Rosenberg, J. T.; Ji, X.; Grant, S. C.; Mattoussi, H. (under review)

TABLE 1

Abbreviations for chemicals

| Abbreviation | Name of chemical |
|---|---|
| PAA | polyacrylic acid |
| PEG | polyethylene glycol |
| TA | thioctic acid |
| DHLA | dihydrolipoic acid |
| DMAP | 4-(N,N-dimethylamino) pyridine |
| DCC | N,N-dicyclohexylcarbodiimide |
| DMF | Dimethyl formamide |

TABLE 2

Relative % of the various PEGylated moieties bound along the PAA backbone.

| Compound | % OCH$_3$-PEG | % TA-PEG | % N$_3$-PEG |
|---|---|---|---|
| 4A | ~64-68 | ~28 | — |
| 4B | ~44-48 | ~44-48 | — |
| 6A | ~40-44 | ~44-48 | ~4-8 |
| 6B | ~32-36 | ~44-48 | ~8-12 |
| 6C | ~40-44 | ~36-40 | ~8-12 |

TABLE 3

Overlap integral, quantum yields, Förster radius/distance, and the estimated number of acceptors in the QD-Pep-Cy3 conjugate.

| Donor-acceptor pair | 543 nm QD-Cy3 |
|---|---|
| Overlap integral, I × 10$^{13}$ (Cm$^3$/M) | 7.61 |
| Quantum yield | 0.25 |
| Förster distance, R$_0$(Å) | 57.3 |
| Number of acceptor(s) | ~20-21 |

That which is claimed is:

1. A composition comprising:
nanoparticles surface-capped with a coating composition, the coating composition comprising:
repeating polyacrylic acid monomer units covalently bound together in an aliphatic chain having a plurality of carboxylic acid functional groups and modified carboxylic acid functional groups extending therefrom, wherein a first portion of the modified carboxylic acid functional groups are modified by a PEG oligomer having a terminal methoxy functional group and a second portion of the modified carboxylic acid functional groups are modified by a PEG oligomer having at least one terminal sulfur moiety.

2. The composition of claim 1, wherein the nanoparticles are coated by being directly bound to the at least one terminal sulfur moiety.

3. The composition of claim 1, wherein the nanoparticles are selected from metallic nanoparticles, semiconductor nanoparticles, or a combination thereof.

4. The composition of claim 1, wherein the nanoparticles are selected from gold nanoparticles, ZnS nanoparticles, CdSe nanoparticles, or a combination thereof.

5. The composition of claim 1, wherein the at least one terminal sulfur moiety is formed from thioctic acid.

6. The composition of claim 1, wherein the at least one terminal sulfur moiety is formed from dihydrolipoic acid.

7. The composition of claim 1, wherein the PEG oligomer having a terminal methoxy functional group is formed from a Compound 2 having a structure:

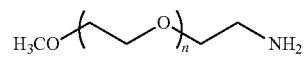

2 wherein n has a value such that an average molecular weight of the PEG oligomer is about 750.

8. The composition of claim 1, wherein the PEG oligomer having at least one terminal sulfur moiety is formed from a Compound 1 having a structure:

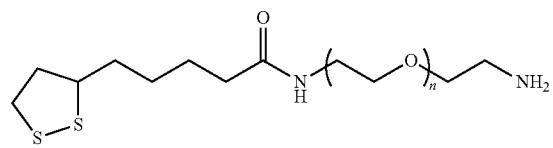

1

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 1

Cys Gly Asn Gly Ile Gln Val Arg Ile Lys Pro Gly Ser Ala Asn
1               5                   10                  15
``` wherein n has a value such that an average molecular weight of the PEG oligomer is about 600.

9. The composition of claim 1, wherein the PEG oligomer having a terminal methoxy functional group is formed from a Compound 2 and the PEG oligomer having at least one terminal sulfur moiety is formed from a Compound 1; wherein the Compound 2 and the Compound 1 have the following structures:

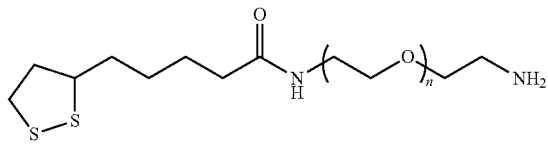

wherein n has a value such that an average molecular weight of the PEG oligomer is about 750; and

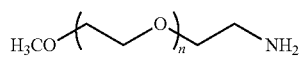

wherein n has a value such that an average molecular weight of the PEG oligomer is about 600.

10. The composition of claim 1, wherein the PEG oligomer having at least one terminal sulfur moiety is formed from dihydrolipoic acid.

11. The composition of claim 1, further comprising a third portion of modified carboxylic acid functional groups, wherein the third portion of the modified carboxylic acid functional groups are modified by a PEG oligomer having a terminal azide functional group.

12. The composition of claim 11, wherein the PEG oligomer having at least one terminal sulfur moiety is formed from a Compound 1 having a structure:

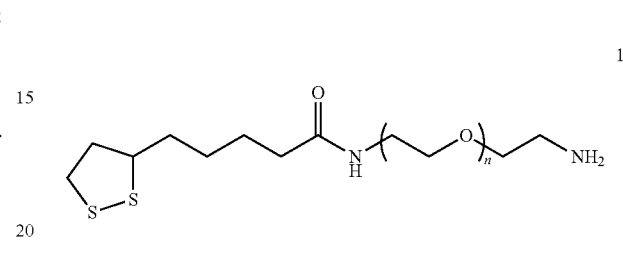

wherein n has a value such that an average molecular weight of the PEG oligomer is about 600.

13. The composition of claim 1, wherein a third portion of the modified carboxylic acid functional groups are modified by a PEG oligomer having a terminal amine functional group.

14. The composition of claim 13, wherein the PEG oligomer having at least one terminal sulfur moiety is formed from dihydrolipoic acid.

* * * * *